(12) United States Patent
Kobold et al.

(10) Patent No.: US 11,099,154 B2
(45) Date of Patent: Aug. 24, 2021

(54) METHOD AND DEVICE FOR SEPARATING METABOLITES OR STEREOISOMERS

(71) Applicants: Roche Diagnostics Operations, Inc., Indianapolis, IN (US); Owlstone Medical Limited, Cambridgeshire (GB)

(72) Inventors: Uwe Kobold, Weilheim (DE); Roland Thiele, Obersoechering (DE); Noah Weiss, Munich (DE); Lauren Brown, Cambridgeshire (GB)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 0 days.

(21) Appl. No.: 15/366,695

(22) Filed: Dec. 1, 2016

(65) Prior Publication Data

US 2017/0082578 A1 Mar. 23, 2017

Related U.S. Application Data

(63) Continuation of application No. PCT/EP2015/062108, filed on Jun. 1, 2015.

(30) Foreign Application Priority Data

Jun. 4, 2014 (EP) .................................... 14171145

(51) Int. Cl.
| | |
|---|---|
| *G01N 27/624* | (2021.01) |
| *G01N 33/82* | (2006.01) |
| *G01N 33/487* | (2006.01) |
| *H01J 49/00* | (2006.01) |

(52) U.S. Cl.
CPC ......... *G01N 27/624* (2013.01); *G01N 33/487* (2013.01); *G01N 33/82* (2013.01); *H01J 49/0031* (2013.01)

(58) Field of Classification Search
USPC ........................................................ 250/282
See application file for complete search history.

(56) References Cited

U.S. PATENT DOCUMENTS

| | | | | |
|---|---|---|---|---|
| 7,662,936 | B2 * | 2/2010 | Kadkhodayan | C07K 16/32 530/413 |
| 8,563,322 | B2 | 10/2013 | Mie et al. | |
| 8,729,463 | B2 * | 5/2014 | Calton | G01N 33/82 250/288 |
| 9,265,772 | B2 * | 2/2016 | Bersot | A61P 25/28 |
| 9,400,261 | B2 * | 7/2016 | Black | G01N 27/624 |
| 2009/0090855 | A1 | 4/2009 | Kobold et al. | |
| 2009/0224147 | A1 | 9/2009 | Mie et al. | |
| 2014/0166875 | A1 * | 6/2014 | Trimpin | H01J 49/04 250/282 |
| 2016/0317553 | A1 * | 11/2016 | Salameh | A61K 31/195 |
| 2018/0282405 | A1 * | 10/2018 | McClain | C07K 16/00 |

FOREIGN PATENT DOCUMENTS

| | | |
|---|---|---|
| EP | 2068143 A1 | 6/2009 |
| WO | 2011/121342 A1 | 10/2011 |
| WO | 2013061146 A1 | 5/2013 |
| WO | 20140/40754 A2 | 3/2014 |

OTHER PUBLICATIONS

Baechler, Silvia et al., Simultaneous quantification of four vitamin D metabolites in human serum using high performance liquid chromatography tandem mass spectrometry for vitamin D profiling, Clinical Biochemistry, 2012, pp. 1491-1496, vol. 45.
Domalain, Virginie et al., Role of Cationization and Multimers Formation for Diastereomers Differentiation by Ion Mobility-Mass Spectrometry, Journal of the American Society for Mass Spectrometry, 2013, pp. 1437-1445, vol. 24.
Dwivedi, Prabha et al., Rapid Resolution of Carbohydrate Isomers by Electrospray Ionization Ambient Pressure Ion Mobility Spectrometry-Time-of-Flight Mass Spectrometry (ESI-APIMS-TOFMS), Journal of the American Society of Mass Spectrometry, 2007, pp. 1163 1175, vol. 18, No. 7.
Fazili, Zia and Pfeiffer, Christine M., Accounting for an Isobaric Interference Allows Correct Determination of Folate Vitamers in Serum by Isotope Dilution-Liquid Chromatography-Tandem MS, The Journal of Nutrition, 2013, pp. 108-113, vol. 143.
Ferreira, Rubén et al., Mass spectrometry and ion mobility spectrometry of G-quadruplexes. A study of solvent effects on dimer formation and structural transitions in the telomeric DNA sequence d(TAGGGTTAGGGT), Methods, 2012, pp. 56-63, vol. 57, No. 1.
Gabryelski, Wojciech and Froese, Kenneth L., Rapid and Sensitive Differentiation of Anomers, Linkage, and Position Isomers of Disaccharides Using High-Field Asymmetric Waveform Ion Mobility Spectrometry (FAIMS), Journal of the American Society of Mass Spectrometry, 2003, pp. 265-277, vol. 14.
International Search Report dated Aug. 12, 2015, in Application No. PCT/EP2015/062108, 5 pps.
Kanu, Abu B. et al., Ion mobility-mass spectrometry, Journal of Mass Spectrometry, 2008, pp. 1-22, vol. 43, No. 1.
Kobold, Uwe, Approaches to measurement of Vitamin D concentrations—Mass spectrometry, Scandinavian Journal of Clinical & Laboratory Investigation, 2012, pp. 54-59, vol. 72, Supplement 243.

(Continued)

*Primary Examiner* — Phillip A Johnston
(74) *Attorney, Agent, or Firm* — Stinson LLP

(57) ABSTRACT

A method of quantifying the amount of at least two analytes A1 and A2 involving (a) adding at least one salt (S) to at least a portion (P1) of the sample comprising the at least two analytes A1 and A2, (b) ionizing at least a portion of the sample according to (a) thereby forming an analyte flow comprising the analytes A1 and A2 in ionized form, (c) separating the ionized analytes A1 and A2 from each other by using at least one ion mobility separator (124), wherein the analyte flow according to (b) at least partially passes through the ion mobility separator (124), and (d) quantifying the amount of the separated ionized analytes obtained according to (c), wherein A1 is a pharmaceutically active compound C or derivative thereof and A2 is a metabolite or stereoisomer of C.

21 Claims, 17 Drawing Sheets

(56) References Cited

OTHER PUBLICATIONS

Koenig, Katrin et al., Deproteination of serum samples for LC-MS/MS analyses by applying magnetic micro-particles, Clinical Biochemistry, 2013, pp. 652-655, vol. 46.

Peters, Frank T. and Remane, Daniela, Aspects of matrix effects in applications of liquid chromatography-mass spectrometry to forensic and clinical toxicology—a review, Analytical and Bioanalytical Chemistry, 2012, pp. 2155-2172, vol. 403.

Hampe, Manfred J., Lösungsmittel-Auswahl bei der Flüssig/Flüssig-Extraktion unter physikalisch-chemischen Aspekten, Chemie Ingenieur Technik, 1985, pp. 669-681, vol. 57, No. 8, Abstract.

* cited by examiner

METHOD AND DEVICE FOR SEPARATING METABOLITES OR STEREOISOMERS

CROSS-REFERENCE TO RELATED APPLICATIONS

This application is a continuation of International Application No. PCT/EP2015/062108 filed Jun. 1, 2015, which claims priority to EP Application No. 14171145.7 filed Jun. 4, 2014, the disclosures of which are hereby incorporated by reference in their entirety.

BACKGROUND OF THE DISCLOSURE

Ion mobility spectrometry has gained attention as approach to analyze gaseous samples for example in ambient atmosphere and drug particles in contact with the skin surface. This technique distinguishes ion species on the basis of the difference in the drift velocity of ions through gas under an applied electric field.

High-Field Asymmetric Waveform Ion Mobility Spectrometry has been proposed, e.g. for the separation of disaccharide and trisaccharide anomers, linkage isomers and position isomers (see Gabryelski W and Froese K. L., American Society of Mass Spectrometry, 2003, 14, 265-277). These water soluble compounds, which differ at least in the stereochemical orientation of at least one sugar moiety or in the position of a residue, such as $O—(CH_2)_8—COOCH_3$, could be qualitatively determined either in the positive ion mode or in the negative ion mode after addition of salts to an aqueous solution comprising the isomers. It is proposed that the saccharide compounds form stable complexes with the cation or anion derived from the salt (depending on whether a positive or negative ionization mode is used), wherein for each sample to be separated the addition of a different salt is reported to be necessary for a resolution of the peaks corresponding to the different isomer. However, despite the considerable differences between the isomers to be analyzed and though these water soluble compounds should easily form complex ions present in the added salt, even at concentration as low as 1 micromolar, only a poor resolution of the peaks corresponding to the different isomers is reported. In particular, no baseline resolution of the isomers was obtained which makes a quantification of the amount of the different compounds difficult or even impossible. A separation or even quantification of epimers of lipophilic or even water insoluble compounds, such as steroids, has, however, not been reported.

There are numerous reasons to monitor pharmaceutical active compounds such as steroids, e.g. steroid hormone levels of an individual. For example, it is often desired to monitor progesterone and/or estrogen levels of women receiving hormone replacement therapy; androgen levels of men treated for prostate cancer; hormone levels of children with pituitary disorders; or progesterone levels of pregnant women. Further, athletes and racehorses are often tested for anabolic steroids. Often, simultaneous and accurate measurements or circulating steroids and their metabolites such as their epimers are desired.

In particular, simultaneous and accurate measurements or circulating vitamin D metabolites are critical to studies of the metabolic regulation of vitamin D and its impact on health and disease. Vitamin D is an essential nutrition with important physiological roles in the positive regulation of calcium homeostasis. Vitamin D can be generated de novo on the skin by exposure to sunlight or it can be absorbed from the diet. Insufficiency or deficiency of vitamin D is a risk factor for metabolic bone diseases such as rickets, osteoporosis, and osteomalacia. Vitamin D exists naturally in two forms, namely vitamin D2 and vitamin D3. The major source of vitamin D in humans is the photoconversion of 7-dihydrocholesterol to pre-vitamin D3 in the epidermis which isomerizes to vitamin D3. Vitamin D3 undergoes 25-hydroxylation by 25-hydroxlyase enzymes in the liver to produce 25-hydroxy vitamin D3. This vitamin D3 is generally believed to be the most abundant form circulating in the body. Alternatively, 25-hydroxy vitamin D3 can be converted into the most biological active form, 1,25-dihydroxy vitamin D3, a reaction predominantly occurring in the kidney. Beside 25-hydroxyvitamin $D_3$ ($25OH-D_3$) and 25-hydroxyvitamin $D_2$ ($25OH-D_2$) the isoform 3-epi-25-hydroxyvitamin $D_3$ ($3$-epi-$25OH-D_3$) and the metabolite 24R,25-dihydroxyvitamin $D_3$ ($24R,25(OH)_2-D_3$) of $25OH-D_3$ have gained more and more attention during the last years. It has been proposed that in particular the plasma concentration of 3-epi-25-hydroxy vitamin D3 relating to that of its epimer should be differentiated to have a better indication of the vitamin D3 status.

However, due to their hydrophobicity and in particular their very high similarity in structure, the separation of 25-hydroxy vitamin D3 and 3-epi-25-hydroxy vitamin D3, which only differ in the stereochemical orientation of one hydroxy group, is very time consuming, expensive and difficult. In particular, HPLC-MS/MS methods have been proposed for the quantification of vitamin D metabolites in serum (see Kobold U, Scandinavian Journal of Clinical & Laboratory Investigations, 2012, 72, 54-59; Baecher et al., Clinical Biochemistry 45 (2012) 1491-1496). However, for such methods very long separation times are necessary due to the high structural similarity of both compounds. In particular, very special columns need to be used which in turn make the method highly expensive and thus disadvantageous for routine applications in clinical settings.

Further, the amount of folate vitamer levels has gained attention. Folate vitamers are important cofactors in 1-carbon metabolism, participating in methylation reactions and DNA synthesis. A suboptimal folate status may modulate chronic diseases such as cardiovascular disease, cancer, and/or cognitive impairment. There is great interest in exploring associations between folate vitamers and health effects. However, the analysis of folates in serum is complex because of numerous folate derivatives that exist in different oxidation states and 1carbon substitutions. Folates are also sensitive to oxidative degradation. Serum 5-methyltetrahydrofolate (5-methylTHF)3, the main circulating folate form, can readily undergo mild reversible oxidation to 5-methyldihydrofolate. Severe or prolonged oxidation can convert 5-methylTHF or 5-methyldihydrofolate to 4a-hydroxy-5-methylTHF, an intermediate product also called hmTHF. In the absence of a reducing agent, hmTHF undergoes structural rearrangement to form a pyrazino-s-triazine derivative. This stable oxidation product of 5-methylTHF is also known as MeFox, the methyl folinate oxidation pro MeFox and 5-formyltetrahydrofolate (5-formylTHF) are isobaric compounds and as such form the same mass to charge (m/z) parent to product ion pairs during ionization, making coelution and mis-identification during liquid chromatography tandem MS (LC-MS/MS) analysis likely (see Fazil an Pfeiffer, Journal of Nutrition, 2β13, 109-119). Similar as the methods proposed for vitamin D measurements, also the methods proposed in view of folate vitamers are not suitable for routine applications in clinical settings.

Further, the measurement of the level of other steroids and their metabolites, such as cortisone or metabolites thereof, such as e.g. the amount of corticosterone, 11-deoxycortisol and 21-deoxycortisol, remains a challenge for the endocrinological community due to the high similarity of the structures and masses of the different metabolites.

Thus, there is still the need for a method for screening pharmaceutically active agents, such as vitamins, steroids or the like and their metabolites or stereoisomers, present in a sample, in particular in a bodily sample which is fast, accurate, easy to perform, cost-effective and in which the amount of the respective analytes may be quantified.

This problem is solved by a method with the features of the independent claims. Preferred embodiments, which might be realized in an isolated fashion or in arbitrary combination, are listed in the dependent claims. Surprisingly, it has been found that despite their similar structure and their low solubility in water, structurally very similar compounds, such as epimers, such as 25-hydroxy vitamin D3 and 3-epi-25-hydroxy vitamin D3, can be accurately quantified by ion mobility spectrometry in the presence of at least one salt.

BRIEF SUMMARY OF THE DISCLOSURE

Provided are methods for quantifying the amount of at least two analytes A1 and A2 comprised in a sample using ion mobility spectrometry, wherein the first analyte A1 is a pharmaceutically active compound C or a derivative thereof and A2 is a metabolite or stereoisomer of C, wherein the method generally comprises the addition of at least one salt to the sample, the ionization of the first analyte and the second analyte, the separation of the ionized first analyte from the ionized second analyte by ion mobility spectrometry and the final quantification of the amount of the respective separated ionized analytes.

DETAILED DESCRIPTION OF THE DISCLOSURE

Figure 1:
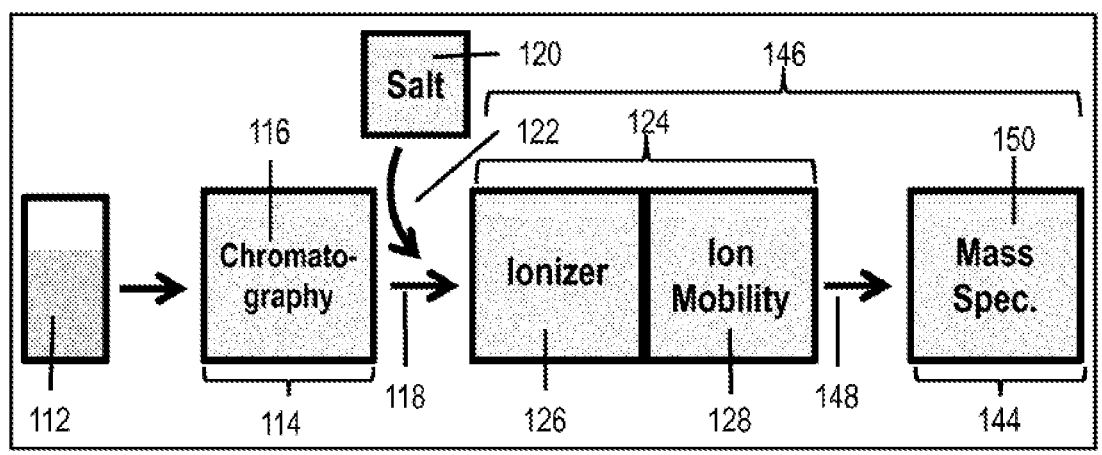
FIG. 1 shows a system for quantifying the amount of at least two analytes in a sample and an exemplary arrangement for performing the method according to the present invention (Example schematic of a System for Analyte Quantification (110))

The present invention relates to a method of quantifying the amount of at least two analytes A1 and A2 comprised in a sample, comprising:
 (a) adding at least one salt (S) to the sample comprising the at least two analytes A1 and A2,
 (b) ionizing at least a portion of the sample according to (a) thereby forming an analyte flow comprising the analytes A1 and A2 in ionized form,
 (c) separating the ionized analytes A1 and A2 from each other by using at least one ion mobility separator, wherein the analyte flow according to (b) at least partially passes through the ion mobility separator,
 (d) quantifying the amount of the separated ionized analytes obtained according to (c),
wherein A1 is a pharmaceutically active compound C or derivative thereof and A2 is a metabolite or stereoisomer of C.

The method steps specifically may be performed in the given order. However, two or more of the method steps may fully or partially be combined to form a combined method step. Further, two or more of the method steps may fully or partially be performed simultaneously. Further, one or more or even all of the method steps may be performed repeatedly or continuously.

Further, the present invention relates to the use of at least one salt (S) as modifier in a process for quantifying the amount of at least two analytes A1 and A2 comprised in a sample by ion mobility spectrometry, wherein A1 is a pharmaceutically active compound C or derivative thereof and A2 is a metabolite or stereoisomer of C.

As used in the following, the terms "have", "comprise" or "include" or any arbitrary grammatical variations thereof are used in a non-exclusive way. Thus, these terms may both refer to a situation in which, besides the feature introduced by these terms, no further features are present in the entity described in this context and to a situation in which one or more further features are present. As an example, the expressions "A has B", "A comprises B" and "A includes B" may both refer to a situation in which, besides B, no other element is present in A (i.e. a situation in which A solely and exclusively consists of B) and to a situation in which, besides B, one or more further elements are present in entity A, such as element C, elements C and D or even further elements.

Further, as used in the following, the terms "preferably", "more preferably", "particularly", "more particularly", "specifically", "more specifically", "in particular" or similar terms are used in conjunction with optional features, without restricting alternative possibilities. Thus, features introduced by these terms are optional features and are not intended to restrict the scope of the claims in any way. The invention may, as the skilled person will recognize, be performed by using alternative features. Similarly, features introduced by "in an embodiment of the invention" or similar expressions are intended to be optional features, without any restriction regarding alternative embodiments of the invention, without any restrictions regarding the scope of the invention and without any restriction regarding the possibility of combining the features introduced in such way with other optional or non-optional features of the invention.

The Analyte A1

As outlined above, A1 is a pharmaceutically active compound C or a derivative thereof. The term "derivative thereof" is not particularly restricted and preferably relates to ester, amide, prodrug or metabolite of C. Thus, preferably, A1 is a pharmaceutically active compound C or ester, amide, prodrug or metabolite. More preferably, A1 is a pharmaceutically active compound C or a metabolite thereof, most preferably, A1 is the pharmaceutically active compound C.

Preferably, compound C is selected from the group consisting of vitamins, hormones, cardiac glycosides, amphetamines, antibiotics, barbiturates, benzodiazepines, cannabinoids, opiates, alkaloids, immunosupressants, steroids, anesthetics, analgesics, antiarrhythmics, psychedelic drugs or drugs of abuse, dissociative, stimulants, anticonvulsants, and tricyclic antidepressants.

Preferably, compound C is selected from the group consisting of vitamins (such as Vitamin D or folate), hormones (such as a steroid hormones), antibiotics (such as glycopeptide antibiotics), and psychedelic drugs or drugs of abuse (such as amphetamines).

According to a particularly preferred embodiment, compound C is a steroid or steroid analogue. The term "steroid" as used within the meaning of the present invention is well known in the art and relates to any type of organic compound that contains a characteristic arrangement of four cycloalkane rings that are joined to each other. The core of steroids is composed of seventeen carbon atoms bonded together that take the form of four fused rings: three cyclohexane rings (designated as rings A, B and C in structure (Ia) below) and one cyclopentane ring (the D ring). The steroids vary by the functional groups attached to this four-ring core and by the oxidation state of the rings. This includes sterols, steroid hormones and derivatives of the aforementioned compounds.

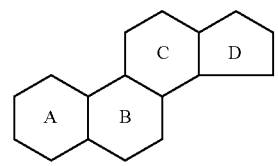

Ia

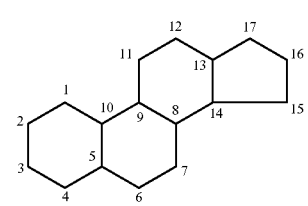

Ib

The term steroid analogue refers to compounds derived from steroids, in particular to secosteroids. The term "secosteroids" refers to compounds containing the A as well as the C and D ring, in which, however, carbon 9 and 10 according to the atom numbering shown in the structure (Ib) above are not linked with each other. These seco-steroids preferably contain a core structure as shown below or stereoisomeric form thereof:

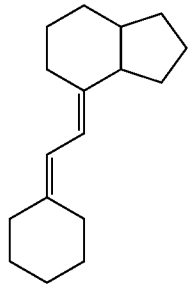 [SMILES: C(/C=C1\CCCC2CCCC12)=C1CCCCC1]

The term "steroid and steroid analogues" includes all human, mammalian, other vertebrate, insect and plant steroids and steroid analogues, as well as synthetic steroids and steroid analogues.

Preferably, the steroid and steroid analogues have a log P value of greater than 0, preferably greater than 2, more preferably greater than 3, more preferably a log P value in the range of from 0 to 12, more preferably in the range of from 2 to 11.5, more preferably in the range of from 3 to 11, wherein the log P value is measured by the distribution behavior of the steroid or the steroid analogue, respectively, in a biphasic system such as in the octanol/water partition test. This test involves the measurement of the equilibrium concentration of a dissolved substance in a two-phase system of an octanol and water as well as a chromatographic method and is described in OECD test guideline 107. The person skilled in the art is aware that log P values can be mathematically predicted by software programs or can be retrieved from databases available to the public (e.g. ACD/Labs Software, ACD/logP www.acdlabs.com, for the prediction of octanol-water partitioning coefficients (log P) from a structure or the Chemspider Database, www.chemspider.com, of the Royal Society of Chemistry to retrieve log P values from a database).

Thus, the present invention relates to a method of quantifying the amount of at least two analytes A1 and A2, as described above, wherein C is a steroid or analogue thereof, preferably having a log P value of greater than 3.0, more preferably a log P value greater than 4.0, more preferably a log P value greater than 4.5 and A2 is an epimer of C. Further, the present invention relates to the use of at least one salt (S) as modifier in a process for quantifying the amount of at least two analytes A1 and A2 comprised in a sample by ion mobility spectrometry, wherein A1 is a steroid or an analogue thereof having a log P value of greater than 3.0, more preferably a log P value greater than 4.0, more preferably a log P value greater than 4.5 and A2 is an epimer of C.

According to a preferred embodiment, C is a steroid hormone (including seco-steroid hormones). Major classes of mammalian steroid hormones include progestagens (progestational hormones), glucocorticoids (anti-stressing hormones), mineralcorticoids (Na+ uptake regulators), androgens (male sex hormones), and estrogens (female sex hormones). Preferred steroids are steroids and steroid anaologues selected from the group consisting of pregnenolone, estrogen (e.g. 17 beta-estradiol), aldosterone, testosterone, androstenedione, progesterone, cortisol, deoxycortisol, corticosterone, dehydroepiandosterone, calcitriol, ecdysone and vitamin D.

Preferably, C is a seco-steroid or a mixture of a seco-steroid and a steroid, preferably a vitamin D. As used herein, the term "a vitamin D" includes any compound being or comprising an analogue of vitamin D. Vitamin D compounds are preferably agonists of the vitamin D receptor. The term "a vitamin D" includes vitamin D1 (which is a mixture of the steroid lumisterol and the seco-steroid ergocalciferol), vitamin D2 (ergocalciferol), vitamin D3 (cholecalciferol or 25-hydroxy vitamin D3), vitamin D5 (22-Dihydroergocalciferol), vitamin D6 (Sitocalciferol), previtamin D3, lumisterol, tachysterol and isomers and/or derivatives (including metabolites) of any one of the aforementioned compounds.

Preferably, C is a seco-steroid being selected from the group consisting of a vitamin D2, a vitamin D3, a vitamin D4, a vitamin D5, previtamin D3, lumisterol, tachysterol and isomers and/or derivatives (including metabolites) of any one of the aforementioned compounds, more preferably, C is a seco-steroid selected from the group consisting of a vitamin D2, a vitamin D3, a vitamin D4, a vitamin D5, previtamin D3, lumisterol and tachysterol, more preferably, C is a seco-steroid selected from the group consisting of a vitamin D3, previtamin D3, lumisterol and tachysterol.

Particularly preferably, C is vitamin D3. The term "a vitamin D3" includes vitamin D3 and metabolites thereof. More preferably, C is vitamin D3, i.e. 25-hydroxy vitamin D3.

Thus, the present invention relates to a method of quantifying the amount of at least two analytes A1 and A2, as described above, wherein A1 is a pharmaceutically active compound C or a derivative thereof with C being a seco-steroid selected from the group consisting of a vitamin D3, previtamin D3, lumisterol and tachysterol, preferably C is 25-hydroxy vitamin D3, and wherein A2 is an epimer of C. Preferably A1 is C. Further, the present invention relates to the use of at least one salt (S) as modifier in a process for quantifying the amount of at least two analytes A1 and A2 comprised in a sample by ion mobility spectrometry, wherein A1 is a pharmaceutically active compound C or a derivative thereof with C being a secosteroid selected from the group consisting of a vitamin D3, previtamin D3, lumisterol and tachysterol, preferably C is 25-hydroxy vitamin D3, and A2 is an epimer of C. Preferably A1 is C.

According to a further particularly preferred embodiment, C is cholesterol or a derivative thereof, such as pregnenolone, 17-alpha-hydroxypregnenolone, dehydroepiandrosterone, androstenediol, progesterone, 17-alpha-hydroxyprogesterone, androstenedione, testosteronedihydrotestosterone, deoxycorticosterone, 11-deoxycortisol, estrone, estradiol, 21-deoxycortisol, cortisol, corticosterone, estriol or the like. Preferably, C is cholesterol. Thus, preferably A1 is cholesterol or a metabolite thereof. Preferably C is cholesterol and A1 is a metabolite of C, preferably corticosterone.

Thus, the present invention also relates to a method of quantifying the amount of at least two analytes A1 and A2, as described above, wherein A1 is C or a metabolite thereof, wherein C is cholesterol, and wherein A2 is a stereoisomer or metabolite of C, preferably a metabolite of C, and wherein A1 is preferably a metabolite of cholesterol, more preferably corticosterone.

According to a further particularly preferred embodiment, C is folate or a derivative thereof, such as 5-methyltetrahydrofolate (5-methylTHF), 5-methyldihydrofolate, 5-methyl-THF, 4a-hydroxy-5-methylTHF, MeFox or 5-formyltetrahydrofolate (5-formylTHF). Preferably, A1 is a metabolite of C with C being folate and A1 being 5-formyltetrahydrofolate, and wherein A2 is preferably a metabolite of C.

Thus, the present invention also relates to a method of quantifying the amount of at least two analytes A1 and A2, as described above, wherein A1 is a metabolite of C, wherein C is a folate and wherein A1 is preferably 5-formyltetrahydrofolate, and wherein A2 is preferably a metabolite of C.

According to a further particularly preferred embodiment, C is a glycopeptide, preferably vancomycin B, CDP-1, CDPM, CDPm a derivative of one of the aforementioned, wherein CDP-1 is a mixture of CDPM and CDPm. CDPM and CDPm are known degradationproducts of vancomycin B. Preferably, A1 is C with C being vancomycin B, and wherein A2 is preferably a metabolite of C.

Thus, the present invention also relates to a method of quantifying the amount of at least two analytes A1 and A2, as described above, wherein C is a glycopeptide, preferably vancomycin B, CDP-1, CDPM or CDPm, more preferably wherein A1 is C with C being vancomycin B, and wherein A2 is preferably a metabolite of C.

According to a further particularly preferred embodiment, C is a psychedelic drug or a drug of abuse. For a list of psychedelic drugs and drugs of abuse reference is made to the SAM-HSA guidlines (Substance abuse and mental health services administration) of the U.S. Department of Health and Human Services (www.samhsa.gov). In an embodiment C is selected from the group consisting of opiates, stimulants, halocinogenes, benzodiazepines, barbiturates and canabinoides. In a particularly preferred embodiment C is an amphetamine. In a further preferred embodiment, A1 is C with C being d-amphetamine-d6. In this case, preferably A2 is being 1-amphetamine-d6. In a further preferred embodiment, A1 is C with C being d-amphetamine ((R)-1-phenylpropan-2-amine) and A2 is being 1-amphetamine ((S)-1-phenylpropan-2-amine).

Thus, the present invention also relates to a method of quantifying the amount of at least two analytes A1 and A2, as described above, wherein A1 is C with C being d-Amphetamine, and wherein A2 is preferably a stereoisomer of C.

The Analyte A2

As outlined above, A2 is a metabolite or stereoisomer of C.

According to a preferred embodiment, A2 is a stereoisomer of C. The term stereoisomer is denoted to mean an isomeric molecule that has the same molecular formula and sequence of bonded atoms (constitution), but that differs only in the three-dimensional orientations of their atoms in space. This includes enantiomers, diastereomers (including epimers), conformers, cis/trans isomers, E/Z-isomers, atropisomers and the like.

Preferably, A2 is an epimer or enantiomer of C. More preferably, A1 is the active compound C and thus A2 is an epimer or enantiomer of A1. The term "epimer" as used herein refers to a compound having the identical chemical formula but a different optical configuration at one particular position, i.e. diastereomers that differ in the configuration of only one stereogenic centre.

In case C is a vitamer D, A2 is preferably an epimer of a vitamin D2, a vitamin D3, a vitamin D4, a vitamin D5, previtamin D3, lumisterol or tachysterol, preferably of vitamin D3, i.e. 25-hydroxy vitamin D3. In particular, A1 is 25-hydroxy vitamin D3 and A2 is 3-epi-25-hydroxy vitamin D3.

Thus, the present invention relates to a method of quantifying the amount of at least two analytes A1 and A2, as described above, wherein A1 is 25-hydroxy vitamin D3 and A2 is 3-epi-25-hydroxy vitamin D3. Further, the present invention relates to the use of at least one salt (S) as modifier in a process for quantifying the amount of at least two analytes A1 and A2 comprised in a sample by ion mobility spectrometry, as described above, wherein A1 is 25-hydroxy vitamin D3 and A2 is 3-epi-25-hydroxy vitamin D3.

It is to be understood that besides the analytes A1 and A2 further analytes present in the sample may be quantified, such as, for example, additionally 25-hydroxyvitamin D2 and the metabolite 24R,25-dihydroxyvitamin D3.

In case C is a psychedelic drug or a drug of abuse, preferably an amphetamine, A2 is preferably a stereoisomer, more preferably an enantiomer or epimer of C. In case A1 is C with C being d-amphetamine, A2 is preferably (S)-1-phenylpropan-2-amine. In case A1 is C with C being d-amphetamine-d6, A2 is preferably 1-amphetamine-d6.

Again, it is to be understood that besides the analytes A1 and A2 further analytes present in the sample may be quantified.

According to an alternative preferred embodiment, A2 is a metabolite of C. The term "metabolite" as used herein, refers to the intermediate or the end products of metabolism.

E.g. in case C is cholesterol or a derivative thereof, A2 is preferably a metabolite of cholesterol. Preferably, A1 is selected from the group consisting of corticosterin, 11-deoxycortisol and 21-deoxycortisol and A2 is selected from the group consisting of corticosterin, 11-deoxycortisol and 21-deoxycortisol, with the proviso that A1 and A2 differ from each other. Again, it is to be understood that besides the analytes A1 and A2 further analytes present in the sample may be quantified.

Further, e.g. in case C is a folate, A2 is preferably a metabolite of C. In this case, preferably, A1 is 5-formyltetrahydrofolate, and A2 is preferably Mefox. Again, it is to be understood that besides the analytes A1 and A2 further analytes present in the sample may be quantified.

E.g. in case A1 is vancomycin B, A2 is preferably a mixture of at least two substances, preferably CDPM and CDPm (=CDP-1). Again, it is to be understood that besides the analytes A1 and A2 further analytes present in the sample may be quantified.

As outlined above, in step (a) according to the invention, at least one salt (S) is added to the sample comprising the at least two analytes A1 and A2.

The term "sample" as used hereinunder and above is not particularly restricted but relates to all possible probes comprising the at least two analytes such as a mixture of the two analytes in a suitable solvent. This includes samples from a body fluid, samples of separate cells or samples from a tissue or an organ as well as samples from foodstuff such as milk or cheese or the like, which e.g. needs to be analysed for their vitamin D content.

Preferably, the sample according to the invention is a sample of or derived from a body fluid, a sample of or derived from separated cells or a sample from a tissue or an organ. Samples of body fluids can be obtained by well-known techniques and include samples of blood, plasma, serum, urine, lymphatic fluid, sputum, ascites, or any other bodily secretion. Tissue or organ samples may be obtained from any tissue or organ by, e.g., biopsy. Separated cells may be obtained from the body fluids or the tissues or organs by separating techniques such as centrifugation or cell sorting. The samples may be frozen, fresh, fixed (including formaline-fixed), centrifuged and/or embedded (e.g. paraffin-embedded). The cells can, of course, be subjected to a variety of well-known post-collection, preparative and storage techniques (e.g. nucleic acid and/or protein extraction, fixation, storage, freezing, ultrafiltration, concentration, evaporation and/or centrifugation or other well-known techniques known to those skilled in the art) prior to quantifying the amounts of the at least two analytes contained in the sample. Likewise, biopsies may also be subjected to post-collection, preparative and storage techniques, e.g. fixation or other techniques known to those skilled in the art.

Thus, the present invention also relates to a method of quantifying the amount of at least analytes A1 and A2 comprised in a sample, as mentioned above, wherein the sample is a sample of a body fluid, a sample of separated cells or a sample from tissue or an organ or a sample derived from any of the aforementioned samples. Preferably, the present invention relates to a method as outlined above wherein the sample is a sample of blood, plasma, serum, urine, lymphatic fluid, sputum, ascites or any other bodily secretion or sample derived from any of the aforementioned samples. Most preferably, the sample is a sample of blood, plasma or serum or a sample derived from blood, plasma or serum.

Preferably, the sample is a sample derived from a raw sample, the raw sample being a sample from a body fluid, a sample of separate cells, a sample from a tissue or an organ, or a sample from foodstuff, preferably, the raw sample is a sample of blood, plasma, serum, urine, lymphatic fluid, sputum, ascites or any other bodily secretion or sample derived therefrom. Most preferably, the raw sample is a sample of blood, plasma or serum.

The term "derived from a raw sample" is denoted to mean that the raw sample is subjected to at least one purification step before performing step (a) to give the sample to be analyzed for its analyte content. Thus, preferably, the method described above comprises at least one additional separation step before performing step (a). Alternatively, the sample in (a) is a raw sample. In this case, preferably, this raw sample is further subjected to at least one purification step either during step (a) or after step (a) but before performing step (b).

Preferably, in the at least one purification step, at least part of the matrix constituents being present in the raw sample are removed. It is to be understood that the term "matrix constituents" within the meaning of the present invention refers to all components in the sample other than the analytes of interest (see Anal Bioanal Chem (2012) 403:2155-2172).

Thus, the present invention relates to a method of quantifying the amount of at least two analytes A1 and A2 comprised in a sample, comprising:
(a) adding at least one salt (S) to the sample comprising the at least two analytes A1 and A2,
(b) ionizing at least a portion of the sample according to (a) thereby forming an analyte flow comprising the analytes A1 and A2 in ionized form,
(c) separating the ionized analytes A1 and A2 from each other by using at least one ion mobility separator, wherein the analyte flow according to (b) at least partially passes through the ion mobility separator,
(d) quantifying the amount of the separated ionized analytes obtained according to (c), wherein A1 is a pharmaceutically active compound C or derivative thereof and A2 is a metabolite or stereoisomer of C, and wherein the sample is a raw sample or a sample derived from a raw sample comprising the analytes A1 and A2 and matrix constituents, and wherein the method further comprises removing at least part of the matrix constituents before, during or after performing step (a), provided that the removal of at least part of the matrix constituents is carried out before performing step (b), preferably, wherein the sample in (a) is derived from a raw sample, and wherein the method further comprises removing at least part of the matrix constituents before performing step (a) to give the sample according to (a).

By way of example, the following matrix constituents are mentioned: Endogenous biological components such as phospholipids, carbohydrates, and endogenous metabolites (e.g. bilirubin), residual formulation components from intraperitoneal (ip), intravenous (iv), or oral dosing (po) experiments; for example, polyethylene glycol (PEG), solutol, polysorbate (Tween 80), etc. and plasma proteins.

The removal may be performed by any method known to those skilled in the art. Preferably, the removal of at least part of the matrix constituents is carried out by at least one of the following methods: centrifugation, filtration, dialysis, protein precipitation (PPT), magnetic particle (bead) separation, by liquid-liquid extraction (LLE), solid phase extraction or by using at least one chromatographic separation step. Combinations of the named methods and/or of other methods known to the skilled person are possible. In case, the at least one purification step is performed during or after step (a), a purification method is chosen which ensures that at least a portion of the salt (S) is comprised or remains in the sample to be ionized in step (b). For example, in case the at least one purification step is performed during step (a) using at least one chromatographic separation step, the mobile phase used in this at least one chromatographic separation step preferably comprises the salt (S).

Protein precipitation may e.g. be carried out by combining a precipitating agent with the raw sample or a sample derived therefrom thereby forming a mixture, preferably subsequent centrifugation of the mixture wherein a sediment and an aqueous solution is obtained, and removal of the sediment from the solution to give, optionally after additional purification steps, the sample employed in step (a) or (b), preferably (a). Commonly acetonitrile (ACN) and/or high concentrated salt solutions and/or alcohols, such as methanol, ethanol, propanol, butanol and the like, are used as precipitating agent(s). As examples, also multiple charged cationic agents such as metal sulfate salts, e.g. zinc sulphate, may be mentioned.

As used herein, the term "liquid/liquid extraction" refers to a process of extraction by adding an aliphatic solvent to the raw sample or the sample derived therefrom. The aliphatic solvent and the raw sample or sample derived therefrom are mixed and separated to form, optionally after additional purification steps, the sample employed in step (a) or (b), preferably (a). As used herein, an aliphatic solvent is comprised of organic molecules having preferably one to twelve carbons, such as hexane, diethylether, chloroform toluene or mixtures of two or more thereof. Suitable solvents are e.g. described Chemie Ingenieur Technik Volume 57, Issue 8, Article first published online: Feb. 2, 2004, http://onlinelibrary.wiley.com/doi/10.1002/cite.330570805/pdf In solid phase extraction, the raw sample or a sample derived therefrom is loaded on a preparatory chromatographic media. The sample comprising the analytes A1 and A2 is then eluted from the preparatory chromatographic media by means of a suitable solvent to form, optionally after additional purification steps, the sample employed in step (a) or (b), preferably (a). The preparatory chromatographic media is chosen depending on the raw sample and analytes A1 and A2. In case A1 is a vitamin D, a polymeric medium is preferred, in particular, a medium based on silica modified by lipophilic surface like RP18, RP8 and the like.

This chromatographic media is preferably contained in a suitable container such as a column, cartridge or a multi-well extraction device.

In a magnetic particle (bead) separation either at least a part of the matrix constituents from the raw sample or a sample derived therefrom are removed by binding to the particles (as described e.g. in Vogeser, M. et al, Clinical Biochemistry 2013, (46) 652-655, EP 2,003,445 or WO 2014/040754) or the magnetic particle (bead) separation is used to enrich the analyte(s) of interest from the raw sample or a sample derived therefrom on the particles, separating and eluating the analyte(s) from the particles (as described in US 2009/0090855 or EP 2,068,143).

As chromatographic separation steps column chromatography, LC, HPLC, ion exchange chromatography, size-exclusion chromatography or gas chromatography, preferably LC, HPLC, ion exchange chromatography or size-exclusion chromatography, should be mentioned.

It is to be understood that two or more of the above mentioned steps may be performed after each other in order to provide the sample employed in step (a). The order of steps is in principle not critical and is chosen depending on the raw sample. Protein precipitation is preferably the first step. Preferably, the at least one purification step is performed before step (a).

Preferably, the method described above comprises at least one solid phase extraction and/or at least one chromatographic separation step, preferably performed before performing step (a), wherein the chromatographic separation step is selected from the group consisting of column chromatography, LC, HPLC, ion exchange chromatography, size-exclusion chromatography or gas chromatography. Suitable conditions and columns for column chromatography, LC, HPLC, ion exchange chromatography, size-exclusion chromatography or gas chromatography are known to those skilled in the art.

Most preferably, the method described above comprises at least one chromatographic separation step before performing step (a), wherein the chromatographic separation step is selected from the group consisting of LC, HPLC and gas chromatography, preferably of LC or HPLC, more preferably HPLC. In case HPLC is carried out, preferably a C4 and/or C18 reversed phase column is employed.

In case at least one separation step is comprised, the at least one separation step may fully or partially be performed before, during or after performing method step (a). As mentioned above, in case a separation step is performed after performing method step (a), the method step generally should be performed such that the at least one salt (S) added in method step (a) at least partially remains within the sample. Thus, preferably, as mentioned above, the at least one separation step generally may be performed at least partially before performing method step (a). As an example, the separation step performed before step (a) is performed in an apparatus or a combination of apparatuses having at least one chromatographic device such as an LC and more preferably an HPLC device and/or a GC device, such as at least one chromatographic device in line with the at least one ion mobility separator. Thus, as an example, the apparatus may be designed such that an output flow of the chromatographic device directly or after passing one or more additional devices enters the ion mobility separator. Additionally or alternatively, an output of the at least one chromatographic device may fully or partially be transferred manually into the ion mobility separator. In between, one or more additional sample preparation steps may be performed, in particular, the addition of the at least one salt which may be performed manually or may be performed in an automated or semi-automated fashion.

Additionally or alternatively, as mentioned above, a purification of the sample, such as a removal of matrix constituents, may be carried out after addition of the salt in (a) and before performing step (b).

As outlined above, in step (a) at least one salt (S) is added to the sample. As outlined above, the adding of the salt (S) may be performed manually, in an automated fashion or in a semi-automated fashion.

The Salt (S)

The salt (S) added in step (a) is preferably the salt of a monovalent or divalent cation or of a monovalent or divalent anion depending on whether the method is carried out in a positive or negative ionization mode. More preferably, the salt (S) added in step (a) is the salt of a monovalent cation or of a monovalent anion.

According to a preferred embodiment, the salt is the salt of a monovalent cation. The term "salt of a monovalent cation" refers to salts comprising a cation with the positive charge +1. The term "salt of a divalent cation" refers to salts comprising a cation with the positive charge +2. Preferably, the salt is a salt of a monovalent cation of an alkaline metal, of a transition metal or of an organic compound. Thus, the present invention also relates to a method described above, wherein the salt is a salt of a monovalent cation being selected from the group consisting of alkaline metal cations, transition metal cations and cations of an organic compound. The term "cation of an organic compound" in particular refers to cations of amines, pyridine, pyrrolidin, imidazole or morpholin. In case the cation is a cation of an organic compound, the cation may e.g. be pyridinium, pyrrolidinium, imidazolium morpholinium or $(R1)(R2)(R3)(R4)N^+$, wherein R1 to R4 may, independently of each other, e.g. be selected from the group consisting of H, alkyl, substituted alkyl, substituted aryl and aryl, such as methyl or H.

More preferably, the salt comprises a cation selected from the group consisting of $Li^+$, $Na^+$, $K^+$, $Rb^+$, $Cs^+$, $Ag^+$, $Cu^+$, $Ni^+$, $Mn^+$, pyridinium and mixtures of two or more thereof. Most preferably the salt (S) comprises a cation selected from the group consisting of $Li^+$, $Na^+$, $K^+$, $Rb^+$, $Cs^+$ and $Ag^+$.

In case C is a vitamer D and A2 is an epimer of C, the salt (S) preferably comprises a cation selected from the group consisting of $Li^+$, $Na^+$, $K^+$, $Cs^+$ and $Ag^+$, more preferably selected from the group consisting of $Na^+$, $K^+$, and $Ag^+$, more preferably the salt (S) comprises the cation K.

In case C is an amphetamine, A2 is preferably a stereoisomer, more preferably an enantiomer or epimer of C, the salt (S) preferably comprises a cation selected from the group consisting of $Li^+$, $Na^+$, $K^+$, $Rb^+$, $Cs^+$ and $Ag^+$, more preferably selected from the group consisting of $Na^+$, $Ag^+$ and $Li^+$, more preferably selected from the group consisting of $Ag^+$ and $Li^+$ more preferably the salt (S) comprises the cation $Ag^+$.

In case C is a steroid and A2 is an isomer, more preferably in case A2 is a mixture comprising at least two isomers selected from list consisting of Corticosterone, 11-deoxycortisol and 21-deoxycortisol, the salt (S) preferably comprises a cation selected from the group consisting of $Li^+$, $Na^+$, $K^+$, $Rb^+$, $Cs^+$ and $A_g+$, more preferably selected from the group consisting of $Na^+$ and $Ag^+$, more preferably the salt (S) comprises the cation $Na^+$. In case C is a steroid preferably a counter current gas flow of the mass spectrometer is enabled (e.g. ABSciex Selex: enabled resolution enhancement). Further, in this case, two molecules C may form with the salt (S) an adduct 2*[C]+[Cation]$^+$, e.g. [2M+Na]$^+$ (e.g. Example 3 and FIG. 9).

In case C is Vancomycin B and A2 is CDPM (Major) and/or CDPm (minor), the salt (S) preferably comprises a cation selected from the group consisting of Li$^+$, Na$^+$, K$^+$, Cs$^+$ and Ag$^+$, more preferably selected from the group consisting of K$^+$, Na$^+$ and Ag$^+$, more preferably the salt (S) comprises the cation K.

In case C is a folate, preferably 5-formyltetrahydrofolate, and A2 is Mefox, the salt (S) preferably comprises a cation selected from the group consisting of Li$^+$, Na$^+$ and K$^+$, more preferably selected from the group consisting of Na$^+$ and Li$^+$, more preferably the salt (S) comprises the cation Li$^+$.

The salt preferably comprises one or more anions selected from the group consisting of fluoride, chloride, bromide, iodide, nitrate, acetate, chlorate, citrate, cyanate, formate, phosphate, oxalate, sulfate, tartrate, carbonate and mixtures of two or more thereof.

Preferably, the salt is selected from the group consisting of lithium fluoride, lithium formate, sodium formate, sodium chloride, sodium acetate, potassium chloride, potassium formate, rubidium acetate, rubidium formate, cesium chloride, cesium formate, silver chloride and silver nitrate.

In case C is a vitamer D and A2 is an epimer of C, the salt (S) the salt is preferably selected from the group consisting of lithium fluoride, lithium formate, sodium formate, sodium chloride, sodium acetate, potassium chloride, potassium formate, cesium chloride, cesium formate, silver chloride and silver nitrate, more preferably selected from the group consisting of lithium formate, sodium acetate, potassium chloride, cesium formate, and silver nitrate, more preferably selected from the group consisting of sodium acetate, potassium chloride, and silver nitrate, more preferably the salt (S) is potassium chloride.

In case C is an amphetamine, A2 is preferably a stereoisomer, more preferably an enantiomer or epimer of C, the salt (S) is preferably selected from the group consisting of lithium fluoride, lithium formate, sodium formate, sodium chloride, sodium acetate, potassium chloride, potassium formate, rubidium acetate, rubidium formate, cesium chloride, cesium formate, silver chloride and silver nitrate, more preferably selected from the group consisting of lithium fluoride, lithium formate, sodium formate, sodium chloride, sodium acetate, silver chloride and silver nitrate, more preferably selected from silver chloride, lithium acetate and sodium acetate, more preferably selected from silver chloride and lithium acetate, more preferably the salt (S) is silver chloride.

In case C is a steroid and A2 is an isomer, more preferably in case A2 is a mixture comprising at least two isomers selected from list consisting of Corticosterone, 11-deoxycortisol and 21-deoxycortisol, the salt (S) is preferably selected from the group consisting of lithium fluoride, lithium formate, sodium formate, sodium chloride, sodium acetate, potassium chloride, potassium formate, rubidium acetate, rubidium formate, cesium chloride, cesium formate, silver chloride and silver nitrate, more preferably selected from the group consisting of sodium formate, sodium chloride, sodium acetate, silver chloride and silver nitrate, more preferably the salt (S) is selected from sodium formate, sodium chloride and sodium acetate.

In case C is Vancomycin B and A2 is CDPM (Major) and/or CDPm (minor), the salt (S) is preferably selected from the group consisting of lithium fluoride, lithium formate, sodium formate, sodium chloride, sodium acetate, potassium chloride, potassium formate, cesium chloride, cesium formate, silver chloride and silver nitrate, more preferably the salt (S) is selected from the group consisting of sodium formate, sodium chloride, sodium acetate, potassium chloride, potassium formate, silver chloride and silver nitrate, more preferably the salt (S) is selected from the group consisting of potassium chloride and potassium formate.

According to a further preferred embodiment, in case the ionization is carried out in the negative mode, the salt (S) is a salt of a monovalent anion. The term "salt of a monovalent anion" refers to salts comprising an anion with the negative charge −1. Preferably, the salt is a salt of a monovalent anion, preferably of a halogen or of an organic compound. As examples, fluorine, chlorine, bromine, iodine, acetate, formate or trifluoroacetate are mentioned.

As to the amount of the added salt (S), preferably the sample according to (a) comprises after addition of the total amount of the salt (S) the added salt (S) in a concentration in the range of from 25 micromol/L to 2 mmol/L, preferably in a concentration in the range of from 40 micromol/L to 1.5 mmol/L, more preferably in a concentration in the range of from 50 micromol/L to 1.0 mmol/L.

Besides the added salt, one or more additional salts such as further monovalent or divalent or trivalent salts may be added.

Preferably, only salts of monovalent ions are added to the sample in step (a). Besides the at least one salt, further additives may be added to the sample in step (a). In particular, additives such as diluents, bases, acids, or buffers should be mentioned.

Preferably, in step (a), at least one diluent, preferably at least one organic solvent, in particular a solvent selected from the group consisting of acetonitrile, methanol, ethanol, propanol and butanol, and mixtures of two or more thereof is added in step (a). Alternatively, the sample according to (a) may already comprise such a diluent, preferably such a solvent. In particular, the sample obtained in (a) comprises methanol.

In an embodiment, the sample according to (a) is additionally acidified by addition of at least one acid. As to the chemical nature of said acid, any acid known to those skilled in the art and being known to be suitable in ion mobility spectrometry may be added. In particular, at least formic acid is added to the sample according to (a).

Preferably, the sample obtained in (a) has a pH in the range of from 1 to 8, more preferably in the range of from 2 to 5, more preferably in the range of from 2 to 4.

In case the sample according to (a) comprises at least one acid, in particular formic acid, acetic acid, propionic acid or TFA (tri-fluor-acetic acid), the amount of acid is preferably in the range of from 1 to 8, more preferably in the range of from 2 to 6, more preferably in the range of from 2 to 5 and most preferably in the range of from 2 to 4, based on the total amount of the sample according to (a).

As suitable buffers, ammonium acetate, formic acid, acetic acid, propionic acid or TFA (tri-fluor-acetic acid), or the corresponding volitaile salts thereof, may be mentioned.

In an embodiment, the sample according to (a) is additionally alkalinized by addition of at least one alkalinizing agent. As to the chemical nature of said alkalinizing agent, any alkalinizing agent known to those skilled in the art and being known to be suitable in ion mobility spectrometry may be added. In particular, at least ammonium hydroxide is added to the sample according to (a).

Preferably, the sample obtained in (a) has a pH in the range of from 4 to 10, more preferably in the range of from 6 to 9, more preferably in the range of from 7 to 8.

In case the sample according to (a) comprises at least one alkalinizing agent, in particular ammonium hydroxide, ammonium carbonate, ammonium hydrogen carbonate or ammonium acetat, the amount of alkalinizing agent is preferably in the range of from 4 to 10, more preferably in the range of from 5 to 9, more preferably in the range of from 6 to 8 and most preferably in the range of from 7 to 8, based on the total amount of the sample according to (a).

As suitable bases, ammonium hydroxide, ammonium carbonate, ammonium hydrogen carbonate or ammonium acetate may be mentioned.

As outlined above, in step (b), at least a portion of the sample according to (a) is ionized thereby forming an analyte flow comprising the analytes A1 and A2 in ionized form. Preferably, in this ionization step, cations of the analytes A1 and A2 are formed. It is contemplated that in the ionization process (step (b)) the analytes form stable complexes with ions derived from the salt.

The ionization in step (b) is carried out by using one or more ionizers. As an example, the at least one ionizer or, in case a plurality of ionizers is used, at least one of the ionizers, may be used for at least partially ionizing the sample in (b), thereby generating the analyte flow, fully or partially before, during or after entering the ion mobility separator. The at least one ionizer may be a separate device and/or may fully or partially be integrated into the at least one ion mobility separator. Thus, step (b) and step (c) may fully or partly be combined. Similarly, as outlined above, one or more ionizers may be used in conjunction with the at least one optional mass spectrometer, as a separate device and/or fully or partially integrated into the mass spectrometer.

The at least one ionizer may be based on generally known ionization techniques and/or may be commercially available. Thus, as an example, one or more of the following devices may be used as the at least one ionizer and/or may be used within the at least one ionizer: an electrospray ionizer; a chemical ionizer such as an atmospheric pressure chemical ionizer (APCI); a photo ionizer, such as one or more of an atmospheric pressure photo ionizer (APPI), an atmospheric pressure laser ionizer (APLI) or matrix-assisted laser desorption/ionization (MALDI). These ionization techniques are generally known to the skilled person, and ionizers based on these ionization techniques are commercially available.

As outlined above, in step (c), the separation of the at least two ionized analytes A1 and A2 takes place by using at least one ion mobility separator, such as at least one ion mobility spectrometer. Therein, the analyte flow, such as a gas flow of a carrier gas and the at least two analytes, at least partially passes through the ion mobility separator.

As used herein and as the skilled person will recognize, an ion mobility separator generally refers to a device adapted for performing a separation of particles, preferably particles in a gas flow or aerosol flow, according to the mobility of the particles. Therein, the mobility generally refers to the ratio of the drift velocity and the electric field. An ion mobility spectrometer generally refers to a measurement apparatus using an ion mobility separator for separating the particles according to their mobility, thereby dividing the particles into at least two mobility classes of particles having the same or similar mobility, and monitoring the number of particles within at least one of the mobility classes.

For separating particles according to their mobility, various ion mobility separation techniques and devices are known to the skilled person. Thus, as an example, one or more techniques or devices may be used, selected from the group consisting of: drift-time ion mobility spectrometry (DTIMS), aspiration ion mobility spectrometry (AIMS), differential mobility analyzer (DMA), travelling-wave ion mobility spectrometry (TWIMS), overtone mobility spectrometry (OMS), field-asymmetric waveform ion mobility spectrometry (FAIMS). Combinations of the named devices and techniques are feasible.

Therein, DTIMS generally refers to a drifting technique in which ions are directed towards a drift tube by a combination of gas flow and electric field. The ions are pulsed into the drift tube by an ion shutter or gate. On entering the drift tube, the ions are subjected to a uniform weak electric field, which accelerates the ions towards a detector situated at the end of the drift tube. An ion passing through a buffer gas, such as a buffer gas within the drift tube, experiences a number of collisions, which impede its progress towards the detector. Larger ions with greater collision cross sections experience more collisions than smaller ions and therefore take longer to traverse the drift tube. Consequently, ions of different shapes and sizes are separated in the drift tube. Since, in most cases, a narrow pulse of ions is typically periodically introduced into the drift region, a duty cycle is typically required which lowers the overall sensitivity and dynamic range of the instrument.

AIMS generally refers to a method in which charged particles are moved by an air stream, or generally a gas stream, into an electrical field which generally is substantially perpendicular to the original direction of movement of the charged particles. Accordingly, the path of the charged particles starts to deviate according to the mass and charge of the charged particles. Clusters with low mobility are driven farther than those with high ion mobility. As a result, a dynamic ion mobility distribution is formed inside the spectrometer. The shape of the distribution of the charged particles is changed when the nature of the sample and/or the sample gas is changed, which in turn changes the differential ion mobilities.

Differential mobility analysis or differential mobility analyzers (DMA) generally are based on an assembly of two concentrically cylindrical electrodes with an air gap between the walls of the electrodes. Air and aerosol flows enter from one end, pass through the annulus and exit the other end. An electric field is applied between the inner and outer electrodes. Particles having a specific mobility exit with the monodisperse air flow through a small slit located at the bottom of the inner electrode. Multi-channel DMAs have also been developed. DMA generally is considered as a distinct technique over FAIMS (also referred to as DMS), since DMA is generally used for classifying and measuring nanometer-sized aerosol particles between 1 nm to 1 µm in diameter, but generally has a poor resolution with aerosols or with particles having a size of less than 100 nm.

TWIMS is generally based on the use of a sequence of ring-shaped electrodes supported on printed circuit boards that deliver both RF and DC voltages. Adjacent rings having opposite phases of Radio Frequency (RF) voltage applied thereto, are used for radially confine in the ions within the device while allowing them to pass unhindered along the axis. A direct current (DC) voltage can be applied to a pair of adjacent rings, to produce a potential barrier that the ions cannot cross. As the DC potential is stepped to an adjacent set of rings the ion barrier moves forward, causing any ions in front of it to be propelled forwards. Stepping the ion barrier sequentially along the rings of the device to the other creates a travelling wave that drives the ions through the device. With the travelling wave ion guide, ions with similar mass to charge (m/z) values, but different charge states, can be separated.

OMS, which was recently developed, generally uses multiple segmented drift regions with modulated linear drift fields to produce conditions that allow only ions with defined mobilities to pass through the instrument. Therefore, the instrument acts as a mobility-filter for continuous ion sources. By changing the frequency of the applied drift fields, it is possible to tune this instrument to transmit ions having different mobilities. A scan over a wide range of drift field frequencies for a single ion species shows a peak corresponding to the expected resonance time of the ions in one drift region segment and a series of peaks at higher frequencies that are overtones of the resonant frequency. Although high resolution can be achieved, OMS generally suffers from low sensitivity in a similar fashion to traditional drift IMS.

FAIMS or DMS generally refers to a technique in which an analyte streamis passed through a slit of two parallel electrodes (drift tube), wherein an electric field is applied across these electrodes. Therein, an asymmetric electric waveform comprised of a short duration, high-voltage (e.g., 10,000 V/cm up to 70,000 V/cm depending on the device used; ABSciex Selexion may use app. 30,000 V/cm) component and a longer duration, low-voltage (e.g., 200 V/cm or ¼ to ⅓ of the magnitude of the high-voltage assuming high-field duty cycle is approx. 25-33%) component, is applied to the parallel electrodes. The separation generally takes place on the basis of the fact that the mobility of ions typically is dependent on the strength of the electric field. Thus, in the FAIMS or DMS device, ions are separated on the basis of the difference in the mobility at high field relative to their mobility at low field. The waveform of the electric field typically is designed such that the voltage-time product for one complete cycle is zero ($V_1T_1+V_2T_2=0$). Ions generally change their mobility in electric fields, e.g. some ions will have a mobility which increases with electric field; other ions have a mobility which decreases with electric field; further ions have a mobility that increases and afterwards decreases in electric field. Typically, the FAIMS or DMS device comprises one or more outlet openings, such as an outlet opening being in straight line with an inlet opening through which the analyte flow enters the FAIMS or DMS device. In order for an ion to exit the FAIMS or DMS device, typically, the ion has to be in a "balanced" condition. The voltage required to create a "balanced" drift for a given ion is generally referred to as the Compensation Voltage (CV or CoV). FAIMS typically offers a high sensitivity separation even at ambient atmospheric pressure and is therefore generally compatible with atmospheric pressure electrospray ionization sources.

Without restricting other commercially available FAIMS devices, SelexION FAIMS devices as commercially available by AB SCIEX, Framingham, Mass., USA, TSQ Quantum™ Access FAIMS devices as commercially available by Thermo Fisher Scientific Inc., Waltham, Mass, USA, or UltraFAIMS devices as commercially available by Owlstone Inc., Norwalk, Conn., USA, may be used.

In the following, due to the above-mentioned advantages, mostly reference is made to ion mobility separators on the basis of FAIMS. It shall be noted, however, that, in addition or alternatively, one or more other ion mobility separation techniques may be used, even though specifically the advantage of atmospheric pressure setups and the use of electrospray ionization sources generally renders FAIMS the preferred technique for the purposes of the present invention.

As outlined above, the ion mobility separator is preferably combined with one or more devices for monitoring an output of the ion mobility separation and the quantification of the analytes.

Thus, as an example, ionization and mobility separation may be combined with techniques of mass spectroscopy. Consequently, step (d) preferably comprises using at least one mass spectrometer for analyzing an output flow of the ion mobility separator.

As used herein, a mass spectrometer generally refers to an apparatus adapted for producing spectra of the masses of particles, such as atoms or molecules, comprising a sample of material. Mass spectrometers generally are based on ionizing the particles, such as chemical compounds, in order to generate charged particles, such as charged molecules or molecular fragments, and measuring their mass-to-charge ratios. Within the mass spectrometer, a sample, such as the output flow of a HPLC seperation and/or particles contained therein, is ionized, such as by spraying the sample through a charged capillary in the presence of an ionic modifier. This treatment may cause some of the sample's particles, such as some of the sample's molecules, to ionize by forming adducts with the ionic modifier. These ions are then separated according to their mass-to-charge ratio, typically by accelerating them and subjecting them to an electric or magnetic field. Within the electric or magnetic field, ions of the same mass-to-charge ratio will typically undergo the same amount of deflection and will not be separated. Besides means for ionizing particles and means for generating the electric field to separate charged ionized particles, mass spectrometers typically further comprise one or more means for detecting the groups of ions having the same mass-to-charge ratio. Thus, as an example, Faraday cups and/or electron multipliers may be used. The results of the separation and detection of ions by mass-to-charge ratio are generally referred to as mass spectra.

The at least one mass spectrometer generally may be any type of mass spectrometer known to the skilled person and/or as commercially available. Thus, as an example, the at least one mass spectrometer may be selected from the group consisting of: a tandem mass spectrometer, an ion trap mass spectrometer, a time-of-flight mass spectrometer, a Fourier transformation mass spectrometer, an orbitrap mass spectrometer, a MALDI mass spectrometer, a quadrupole mass spectrometer. These types of mass spectrometers are generally known to the skilled person and are commercially available in a wide variety by a plurality of vendors.

Thus, the method according to the present invention may comprise using an apparatus having a combination of at least one ion mobility separator and at least one mass spectrometer. The ion mobility separator and the mass spectrometer may be in line, such that the output flow of the ion mobility separator fully or partially, directly or after passing one or more additional devices, may enter the mass spectrometer. The ion mobility separator and the mass spectrometer may be separate devices, which may be linked by a line. Additionally or alternatively, the ion mobility separator and the mass spectrometer may fully or partially be combined, such as by combining the ion mobility separator and the mass spectrometer into a common housing.

The quantification of analytes A1 and A2 in the sample is preferably carried out by comparing the analytical signal, with the signals of a calibration signal and/or curve. Therefore, it is preferred to at least once establish a calibration curve which represents the relationship between the analytical signal obtained from the particular analytical method used in (d), e.g., peak area or peak height in MS spectra or in mass chromatograms, and the quantity of the respective analyte. Thus, prior to the analysis of a sample, preferably the analytical signals of a series of calibration standards (e.g., the isolated analyte in different concentrations) are determined. This type of calibration is generally known to the skilled person in the field of analytics or diagnostics.

Summarizing the findings of the present invention, the following embodiments are preferred:

1. A method of quantifying the amount of at least two analytes A1 and A2 comprised in a sample, comprising:
   (a) adding at least one salt (S) to at least a portion (P1) of the sample comprising the at least two analytes A1 and A2,
   (b) ionizing at least a portion of the sample according to (a) thereby forming an analyte flow comprising the analytes A1 and A2 in ionized form,
   (c) separating the ionized analytes A1 and A2 from each other by using at least one ion mobility separator, wherein the analyte flow according to (b) at least partially passes through the ion mobility separator,
   (d) quantifying the amount of the separated ionized analytes obtained according to (c),
   wherein A1 is a pharmaceutically active compound C or a derivative thereof and A2 is a metabolite or stereoisomer of C.
2. The method according to the preceding embodiment, wherein A1 is a pharmaceutically active compound C or an ester, amide, prodrug or metabolite or, preferably A1 is a pharmaceutically active compound C or a metabolite thereof.
3. The method according to any one of the preceding embodiments, wherein A1 is a pharmaceutically active compound C and A2 is an epimer thereof.
4. The method according to any one of the preceding embodiments, wherein C is selected from the group consisting of vitamins, hormones, cardiac glycosides, amphetamines, antibiotics, barbiturates, benzodiazepines, cannabinoids, opiates, alkaloids, immuno-supressants, steroids, anesthetics, analgesics, antiarrhythmics, psychedelic drugs or drugs of abuse, dissociative, stimulants, anticonvulsants, and tricyclic antidepressants.
5. The method according to any one of the preceding embodiments, wherein C is selected from the group consisting of vitamins (such as Vitamin D or folate), hormones (such as a steroid hormones), antibiotics (such as glycopeptide antibiotics), and psychedelic drugs or drugs of abuse (such as amphetamines).
6. The method according to the preceding embodiment, wherein A1 has a log P value of greater than 0, preferably greater than 2, more preferably greater than 3, in the range of from 0 to 12, more preferably in the range of from 2 to 11.5, more preferably in the range of from 3 to 11.
7. The method according to any one of the preceding embodiments, wherein A1 is a vitamin D, preferably 25-hydroxy-vitamin D3.
8. The method according to the preceding embodiment, wherein A2 is 3-epi-25-hydroxy vitamin D3.
9. The method according to any one of the preceding embodiments, wherein the sample is a sample of a bodily fluid, a sample of separated cells, a sample from tissue of an organ, a sample of foodstuff or a sample derived from any of the aforementioned samples.
10. The method according to any one of the preceding embodiments, wherein the sample is a sample of blood, plasma, serum, urine, lymphatic fluid, sputum, ascites, or any other bodily secretion or a sample derived from any of the aforementioned samples.
11. The method according to any one of the preceding embodiments, and wherein the sample is derived from a raw sample comprising the analytes A1 and A2 and matrix constituents, and wherein the method further comprises removing at least part of the matrix constituents before performing step (a) to give the sample according to (a).
12. The method according to the preceding embodiment, wherein the raw sample is a sample of a bodily fluid, a sample of separated cells or a sample from tissue of an organ or a sample derived from any of the aforementioned samples.
13. The method according to any one of the two preceding embodiments, wherein the raw sample is a sample of blood, plasma or serum.
14. The method according to any one of the three preceding embodiments, wherein the removal of at least part of the matrix constituents is carried out by at least one chromatographic separation step.
15. The method according to any one of the two preceding embodiments, wherein the chromatographic separation step comprises using at least one of a liquid chromatographic separation step or a gas chromatographic separation step.
16. The method according to any one of the preceding embodiments, wherein the salt (S) is a salt of a monovalent cation or monovalent anion.
17. The method according to any one of the preceding embodiments, wherein the salt (S) is a salt of a monovalent cation of an alkaline metal, of a transition or of an organic compound.
18. The method according to any one of the preceding embodiments, wherein the cation is selected from the group consisting of a cation of $Li^+$, $Na^+$, $K^+$, $Rb^+$, $Cs^+$, $Ag^+$, $Cu^+$, $Ni^+$, $Mn^+$, pyridinium and mixtures of two or more thereof, more preferably the cation is selected from the group consisting of $Li^+$, $Na^+$, $K^+$, $Rb^+$, $Cs^+$ and $Ag^+$.
19. The method according to any one of the preceding embodiments, wherein C is a vitamer D and A2 is an epimer of C, any wherein the cation is selected from the group consisting of $Li^+$, $Na^+$, $K^+$, $Cs^+$ and $Ag^+$, more preferably selected from the group consisting of $Na^+$, $K^+$, and $Ag^+$, more preferably cation is $K^+$.
20. The method according to any one of the preceding embodiments, wherein C is an amphetamine, A2 is preferably a stereoisomer, more preferably an enantiomer or epimer of C, and wherein the cation is selected from the group consisting of $Li^+$, $Na^+$, $K^+$, $Rb^+$, $Cs^+$ and $Ag^+$, more preferably selected from the group consisting of $Na^+$, $Ag^+$ and $Li^+$, more preferably selected from the group consisting of $Ag^+$ and $Li^+$ more preferably the cation is $Ag^+$.
21. The method according to any one of the preceding embodiments, wherein C a steroid and A2 is an isomer, more preferably in case A2 is a mixture comprising at least two isomers selected from list consisting of Corticosterone, 11-deoxycortisol and 21-deoxycortisol, and wherein the cation is selected from the group consisting of $Li^+$, $Na^+$, $K^+$, $Rb^+$, $Cs^+$ and $Ag^+$, more preferably selected from the group consisting of $Na^+$ and $Ag^+$, more preferably the cation is $Na^+$.
22. The method according to any one of the preceding embodiments, wherein C is Vancomycin B and A2 is CDPM (Major) and/or CDPm (minor), any wherein the cation is selected from the group consisting of Li$^+$, Na$^+$, K$^+$, Cs$^+$ and Ag$^+$, more preferably selected from the group consisting of K$^+$, Na$^+$ and Ag$^+$, more preferably the cation is K$^+$.

23. The method according to any one of the preceding embodiments, wherein C is a folate, preferably 5-formyltetrahydrofolate, and A2 is Mefox, any wherein the cation is selected from the group consisting of Li$^+$, Na$^+$ and K$^+$, more preferably selected from the group consisting of Na$^+$ and Li$^+$, more preferably the cation is Li$^+$.

24. The method according to any one of the preceding embodiments, wherein the salt (S) is selected from the group consisting of lithium fluoride, lithium formate, sodium formate, sodium chloride, sodium acetate, potassium chloride, potassium formate, rubidium acetate, rubidium formate, cesium chloride, cesium formate, silver chloride and silver nitrate.

25. The method according to any one of the preceding embodiments, wherein C is a vitamer D and A2 is an epimer of C, and wherein the salt (S) is preferably selected from the group consisting of lithium fluoride, lithium formate, sodium formate, sodium chloride, sodium acetate, potassium chloride, potassium formate, cesium chloride, cesium formate, silver chloride and silver nitrate, more preferably selected from the group consisting of lithium formate, sodium acetate, potassium chloride, cesium formate, and silver nitrate, more preferably selected from the group consisting of sodium acetate, potassium chloride, and silver nitrate, more preferably the salt (S) is potassium chloride.

26. The method according to any one of the preceding embodiments, wherein C is an amphetamine, A2 is preferably a stereoisomer, more preferably an enantiomer or epimer of C, and wherein the salt (S) is selected from the group consisting of lithium fluoride, lithium formate, sodium formate, sodium chloride, sodium acetate, potassium chloride, potassium formate, rubidium acetate, rubidium formate, cesium chloride, cesium formate, silver chloride and silver nitrate, more preferably selected from the group consisting of lithium fluoride, lithium formate, sodium formate, sodium chloride, sodium acetate, silver chloride and silver nitrate, more preferably selected from silver chloride, lithium acetate and sodium acetate, more preferably selected from silver chloride and lithium acetate, more preferably the salt (S) is silver chloride.

27. The method according to any one of the preceding embodiments, wherein C is a steroid and A2 is an isomer, more preferably A2 is a mixture comprising at least two isomers selected from list consisting of Corticosterone, 11-deoxycortisol and 21-deoxycortisol, and wherein the salt (S) is selected from the group consisting of lithium fluoride, lithium formate, sodium formate, sodium chloride, sodium acetate, potassium chloride, potassium formate, rubidium acetate, rubidium formate, cesium chloride, cesium formate, silver chloride and silver nitrate, more preferably selected from the group consisting of sodium formate, sodium chloride, sodium acetate, silver chloride and silver nitrate, more preferably the salt (S) is selected from sodium formate, sodium chloride and sodium acetate.

28. The method according to any one of the preceding embodiments, wherein C is Vancomycin B and A2 is CDPM (Major) and/or CDPm (minor), and wherein the salt (S) is selected from the group consisting of lithium fluoride, lithium formate, sodium formate, sodium chloride, sodium acetate, potassium chloride, potassium formate, cesium chloride, cesium formate, silver chloride and silver nitrate, more preferably the salt (S) is selected from the group consisting of sodium formate, sodium chloride, sodium acetate, potassium chloride, potassium formate, silver chloride and silver nitrate, more preferably the salt (S) is selected from the group consisting of potassium chloride and potassium formate.

29. The method according to any one of the preceding embodiments, wherein the sample according to (a) comprises the added salt (S) in a concentration in the range of from 25 micromol/L to 2 mmol/L, preferably in a concentration in the range of from 40 micromol/L to 1.5 mmol/L, more preferably in a concentration in the range of from 50 micromol/L to 1.0 mmol/L.

30. The method according to any one of the preceding embodiments, wherein in (a) at least one further additive is added, preferably an additive selected from the group consisting of acetonitrile, methanol, ethanol, propanol and butanol.

31. The method according to any one of the preceding embodiments, wherein in (a) at least one acid, preferably formic acid, is additionally added.

32. The method according to any one of the preceding embodiments, wherein step (b) comprises using at least one ionizer.

33. The method according to the preceding embodiment, wherein the ionizer is used for at least partially ionizing the sample and thereby generating the analyte flow before or during entering the ion mobility separator.

34. The method according to any one of the two preceding embodiments, wherein the ionizer comprises at least one device selected from the group consisting of: an electrospray ionizer, a chemical ionizer, a photo ionizer.

35. The method according to any one of the preceding embodiments, wherein the ion mobility separator is a field-asymmetric waveform ion mobility separator.

36. The method according to any one of the preceding embodiments, wherein the ion mobility separator comprises at least one ion mobility spectrometer or wherein the ion mobility separator is part of at least one ion mobility spectrometer.

37. The method according to the preceding embodiment, wherein the ion mobility spectrum spectrometer comprises at least one field-asymmetric waveform ion mobility spectrometer.

38. The method according to any one of the preceding embodiments, wherein step (c) further comprises using at least one mass spectrometer for analyzing an output flow of the ion mobility separator.

39. The method according to the preceding embodiment, wherein the mass spectrometer comprises one or more of: a tandem mass spectrometer, an ion trap mass spectrometer, a time-of-flight mass spectrometer, a Fourier transformation mass spectrometer, an orbitrap mass spectrometer, a quadrupole mass spectrometer.

40. The method according to any one of the preceding embodiments, wherein the salt (S) is a salt of a monovalent anion of a halogen or of an organic compound.

41. The method according to any one of the preceding embodiments, wherein the salt is fluorine, chlorine, bromine, iodine, acetate, formate or trifluoroacetate salt.

42. Use of at least one salt (S) as modifier in a process for quantifying the amount of at least two analytes A1 and A2 comprised in a sample by ion mobility spectrometry, wherein A1 is a pharmaceutically active compound C or a derivative thereof and A2 is a metabolite or stereoisomer of C.

43. Method of using at least one salt (S) as modifier in a process for quantifying the amount of at least two analytes A1 and A2 comprised in a sample by ion mobility spectrometry, wherein A1 is a pharmaceutically active compound C or a derivative thereof and A2 is a metabolite or stereoisomer of C, and
wherein A1 has a log P value in the range of from 0 to 12.

Further optional features and embodiments of the invention will be disclosed in more detail in the subsequent description of preferred embodiments. Therein, the respective optional features may be realized in an isolated fashion as well as in any arbitrary feasible combination, as the skilled person will realize. The scope of the invention is not restricted by the preferred embodiments. The embodiments are schematically depicted in the Figures. Therein, identical reference numbers in these Figures refer to identical or functionally comparable elements.

DETAILED DESCRIPTION OF THE EMBODIMENTS

In FIG. 1, an exemplary embodiment of a system 110 for quantifying the amount of at least two analytes in a sample and, thus, an arrangement which may be used for performing the method according to the present invention is schematically depicted. In the setup, a raw sample 112 is provided, such as a chemical raw sample derived from a chemical production process or a biological raw sample, such as a sample of a body fluid like blood, interstitial fluid, saliva, urine, plasma, tear fluid or combinations thereof.

In a second, optional step, the raw sample 112 may be subjected to one or more sample preparation processes, such as by using one or more sample preparation devices 114. As an example, the one or more sample preparation devices 114 may comprise one or more chromatographic devices 116, such as one or more LC and/or GC devices. In the exemplary embodiment shown in FIG. 1, a column chromatographic device and/or a HPLC chromatographic device may be used. As an output of the one or more sample preparation devices 114 and/or as an output of the one or more sample preparation processes a sample 118 is generated.

Further, one or more salts 120 are added to the sample 118. The step of addition of salt 120 is denoted by reference number 122 in FIG. 1, corresponding to step (a) of the method according to the present invention. The addition of salt 120 may fully or partially take place in a manual fashion and/or may take place fully or partially in an automated fashion, such as by using one or more dispensing or dosing devices for adding the salts to the sample 118. The salt addition preferably takes place in a controlled fashion.

The sample 118 with the salt 120 added is, manually or automatically, fully or partially, transferred to an ion mobility separator 124. The transfer, as an example, may take place by using a carrier gas, such as by diluting the sample 118 in the carrier gas and/or by spraying the sample 118 into the carrier gas, preferably by using a nebulizer, an atomizer or a sprayer.

The ion mobility separator 124, in the exemplary embodiment depicted in FIG. 1, comprises an ionizer 126 which, in the embodiment shown, may e.g. be an electrospray ionizer (ESI). The electrospray ionizer may both fulfill the purpose of fully or partially ionizing the sample 118 and/or particles contained therein and the purpose of spraying the sample 118, in a fully or partially ionized fashion, into a differential mobility spectrometer DMS, such as a field-asymmetric waveform ion mobility spectrometry (FAIMS) device 128.

The basic functionality of the FAIMS device 128 will be explained with reference to FIGS. 2(A) and 2(B) below. Therein, FIG. 2(A) shows a schematic cross-sectional view of the FAIMS device 128, and FIG. 2(B) shows an exemplary embodiment of the strength of an electric field E (denoted by reference number 130 and directed in a downward fashion in FIG. 2(A)) as a function of time t.

As can be seen in FIG. 2(A), a sample enters a chamber through a slit of two parallel electrodes (drift tube) 132 through an entry opening 134 and passes the electric field from the left to the right in FIG. 2(A). As depicted in FIG. 2(B), the electric field E as applied to the parallel electrodes 134 has an asymmetrical electrical waveform. Therein, short high-voltage periods 134 and longer low-voltage periods 136 are arranged in an alternating fashion, with the electric field in the high-voltage periods 134 being directed in an opposite direction as compared to the electric field in the low-voltage periods 136. As an example, an asymmetric electric waveform comprised of a short duration, (e.g., 10,000 V/cm up to 70,000 V/cm depending on the device used) may be used in the high-voltage periods 134 and a longer duration, low-voltage period 136 (e.g., 200 V/cm or ¼ to ⅓ of the magnitude of the high-voltage assuming high-field duty cycle is approx. 25-33%) may be used. Typically, the absolute value of the electric field strength in the high-voltage periods may be at least 1.2 times the absolute value of the electric field strength in the low-voltage periods, more preferably at least 1.5 times the absolute value of the electric field strength in the low-voltage periods and more preferably at least 2.0 times the absolute value of the electric field strength in the low-voltage periods. Thus, as an example, the absolute value of the electric field strength in the high-voltage periods may be 1.5 to 100 times the absolute value of the electric field strength in the low voltage periods. The waveform as depicted in FIG. 2(B) generally may be a periodic asymmetric signal, such as an asymmetric rectangular signal. The duration $t_1$ of the high-voltage periods 134 preferably is shorter than the duration $t_2$ of the low-voltage periods 136, such as by a factor of 1.5 to 100. As an example, the duration $t_1$ may be 2 µs, and the duration $t_2$ may be 4 µs. Other waveforms are possible. In case periodic signals are used, the periodic signals, as an example, may have a frequency of 10 Hz to 1 kHz, such as 50 Hz to 500 Hz, e.g. 150 to 200 Hz. Other waveforms, other frequencies, other electric fields and other durations of the high-voltage and low-voltage periods are feasible.

The separation within the drift tube 132 generally takes place on the basis of the fact that the mobility of ions typically is dependent on the strength μ of the electric field. Thus, in the FAIMS or DMS drift tube, ions are separated on the basis of the difference in the mobility at high field relative to their mobility at low field. The waveform of the electric field typically is designed such that the voltage-time product for one complete cycle (i.e. one high-voltage period 134 and one subsequent low-voltage period 136 or vice versa) is zero: $V_1 t_1 + V_2 t_2 = 0$, wherein $V_1$ denotes the voltage during the high-voltage period 134 and wherein $V_2$ denotes the voltage during the low-voltage period 136. As outlined above, the mobility of the ions generally is dependent on the strength of the electric field. Some ions generally will have a mobility which increases with electric field; other ions have a mobility which decreases with field.

Typically, the drift tube 132 comprises one or more outlet openings 138, such as an outlet opening 138 being in straight line with the inlet opening 134. In order for an ion to exit the drift tube 132 through the outlet opening 138, typically, the ion has to be in a "balanced" condition. The voltage required to create a "balanced" drift for a given ion is generally referred to as the Compensation Voltage (CV or CoV). In FIG. 2(A), a drift path 140 of an unbalanced ion, which will not reach the outlet opening 138, and a drift path 142 of a balanced ion, which will reach the outlet opening 138 and will leave the drift tube 132 through the outlet opening 158, are shown. By varying the parameters of the FAIMS device 128, specifically by varying the electrical parameters as shown in FIG. 2(B), such as the waveform of the electric field, the mobility of the balanced ions may be chosen and, by varying one or more of these parameters, a scan through various classes of mobilities may be performed. Thus, the FAIMS device 128 may either be used for particle classification, thereby selecting a specific class of particles from the analyte flow, or may be used for scanning and taking spectra of the particle mobilities contained within the analyte flow.

As outlined above, the ion mobility separator 124 may generally be combined with one or more devices 144 for monitoring an output of the ion mobility separator 124. The combination of the device 144 and the ion mobility separator 124 may generally be referred to as an ion mobility spectrometer 146, wherein, in some cases, the ionizer 126 is also referred to as a part of the ion mobility spectrometer 146. Thus, as an example, when using a FAIMS device 128, the ion mobility spectrometer 146 may be a FAIMS spectrometer.

The device 144 for monitoring the output or output flow 148 of the ion mobility separator 124 may be a simple counting device or may, as depicted in FIG. 1, contain one or more further separating devices. Thus, as an example, device 144 may be or may comprise one or more mass spectrometers 150. As an example, a tandem mass spectrometer may be used.

Figure 2:
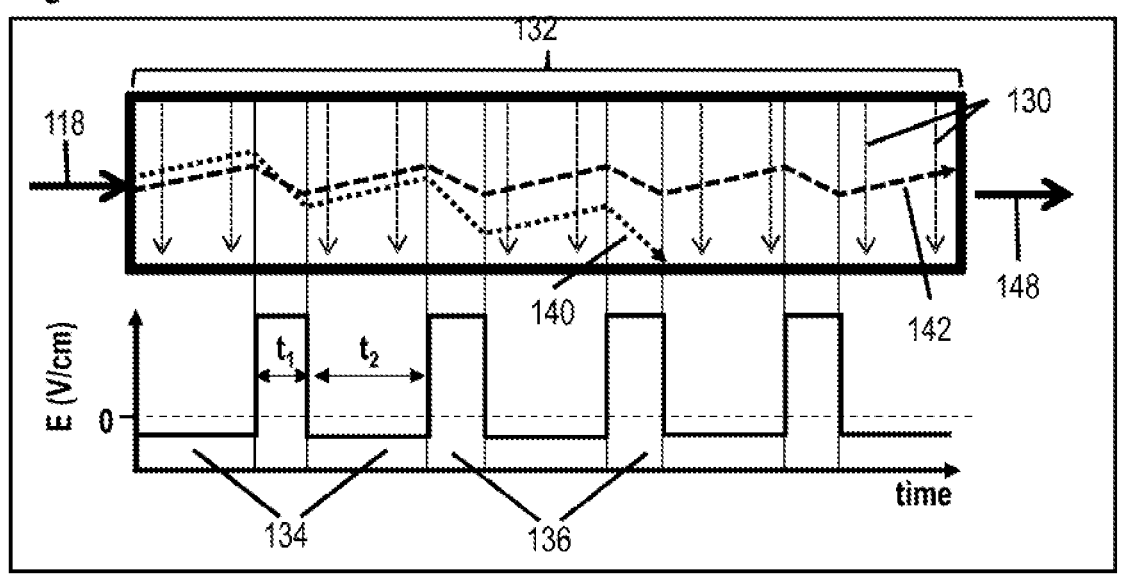
FIG. 2 shows a schematic setup of a field-asymmetric waveform ion mobility spectrometer (FAIMS; part (A)) and of an electric field used therein (part (B)) (Schematic of a FAIMS Device (128)).

It shall be noted that the experimental setup shown in FIGS. 1 and 2 merely is an exemplary setup which, however, was used during the experiments shown in further detail below. Therein, commercially available components were used. Details of the manufacturers and exemplary embodiments of devices and device parameters will be given below. Even though astonishing results were used with the given experimental setup and the parameters, it shall be noted that other devices and parameters may be used.

EXAMPLES

Example 1

Vitamin D (Analysis with UltraFAIMS

A solution of stock solution of 1 mg 25-Hydroxy-Vitamin D3 (25-Hydroxycholecalciferol) (Sigma Aldrich) and a stock solution of 1 mg of 3-epi-25-Hydroxyvitamin D3 (Isosciences LLC) in 1 mL solvent (Methanol: Water=8:2 with 0.1% formic acid) was prepared.

The stock solutions were diluted and optionally mixed to give solutions comprising the amount of 25-Hydroxy-Vitamin D3 and/or 3-epi-25-Hydroxyvitamin D3 as indicated in Table 1. These solutions were containing an amount of sodium salt in the range of app. 25 μM to 100 μM (see examples 1.1-1.6).

The analysis of this solution was performed with an Agilent 6230 TOF MS fitted with Agilent Jet Stream ESI source. The source was operated under the following conditions; capillary voltage 3500 V; Nozzle voltage 2000 V; Sheath gas flow 12 L/min at 250° C.; Nebuliser pressure 15 psig; Drying gas 7 L/min at 125° C. The TOF MS acquired spectra at a rate of 10 spectra/s. Notable ion optics settings were: Fragmentor 175 V; Skimmer 69 V; Oct RF Vpp 750 V.

The FAIMS chip used for the analysis had 100 micron electrode gap, 700 micron device thickness and 97 mm trench length. A chip region temperature estimate of 125° C. was used. The carrier gas used was nitrogen. The FAIMS was scanned over −5 to +5 Td in 0.05 Td steps.

Figure 4:
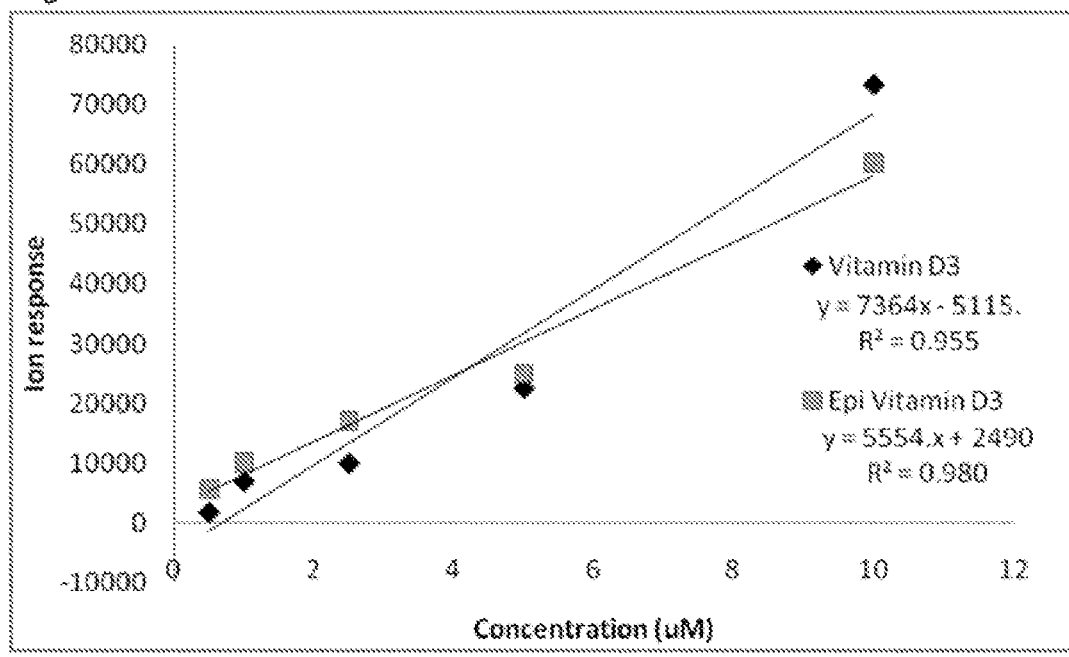
FIG. 4 shows the calibration curve of 3-epi-25-Hydroxyvitamin D3 (Epi Vitamin D3, ■) and 25-Hydroxyvitamin D3 (Vitamin D3, ♦), respectively, wherein the x-axis shows the analyte concentration in micromol and the y-axis shows the respective ion response in counts.

For quantification, calibration curves were prepared. Thus, solutions of 25-Hydroxy-Vitamin D3 were prepared in the following concentrations 0.5 micromolar, 1 micromolar, 2.5 micromolar, 5 micromolar and 10 micromolar. Likewise, solutions of 3-epi-25-Hydroxyvitamin D3 were prepared in the following concentrations 0.5 micromolar, 1 micromolar, 2.5 micromolar, 5 micromolar and 10 micromolar. Each sample was measured separately and based on the results, calibration curves for both components were prepared as shown in FIG. 4 (3-epi-25-Hydroxyvitamin D3 (■), and 25-Hydroxyvitamin D3(♦)).

For the purpose of measurement by ion mobility separation, the ion mobility spectrometer of the "UtraFAIMS" type was used, commercially available by Owlstone Inc., Norwalk, Conn., USA. UltraFAIMS is a chip-based FAIMS platform designed to interface with a Mass Spectrometer to provide additional in-source separation of ions. The core of the ultraFAIMS platform is a microchip-sized FAIMS spectrometer that allows the selective transmission of ions based on differences in the way their mobility varies in a changing electric field. The Ultra-FAIMS chip has a small footprint of approx. 2 mm thickness and 17 mm in diameter and can be floated to 6 kV, which means it can be interfaced with most mass spectrometers. In the setup used for the present experiments, the UltraFAIMS apparatus was combined with an Agilent Jetstream electrospray ionization source and an Agilent 6230 TOF mass spectrometer. In this FAIMS-MS setup, the FAIMS device was used as a tunable filter, allowing certain ions to be transmitted to the mass spectrometer while blocking others.

Further details are given in the following table 1:

TABLE 1

| Example | Concentration of 25-Hydroxy-Vitamin D3 [micromol/L] | Concentration 3-epi-25-Hydroxy-Vitamin D3 [micromol/L] | Sodium salt app. 25-100 μM | Water [Vol %] (based on the total volume of the sample) | Methanol [Vol %] (based on the total volume of the sample) | Formic acid [Vol %] (based on the total volume of the sample) | Townsend [Td] | See FIG. |
|---|---|---|---|---|---|---|---|---|
| 1.1 (a) | 2.5 | — | trace | 20 | 80 | 0.1 | 280 | 3 |
| 1.1 (b) | — | 2.5 | trace | 20 | 80 | 0.1 | 280 | 3 |
| 1.2 | 1.25 | 0 | trace | 20 | 80 | 0.1 | 280 | 5 |
| 1.3 | 1.25 | 0.125 | trace | 20 | 80 | 0.1 | 280 | 5 |
| 1.4 | 1.25 | 0.25 | trace | 20 | 80 | 0.1 | 280 | 5 |
| 1.5 | 1.25 | 0.5 | trace | 20 | 80 | 0.1 | 280 | 5 |
| 1.6 | 1.25 | 1.25 | trace | 20 | 80 | 0.1 | 280 | 5 |

Figure 3:
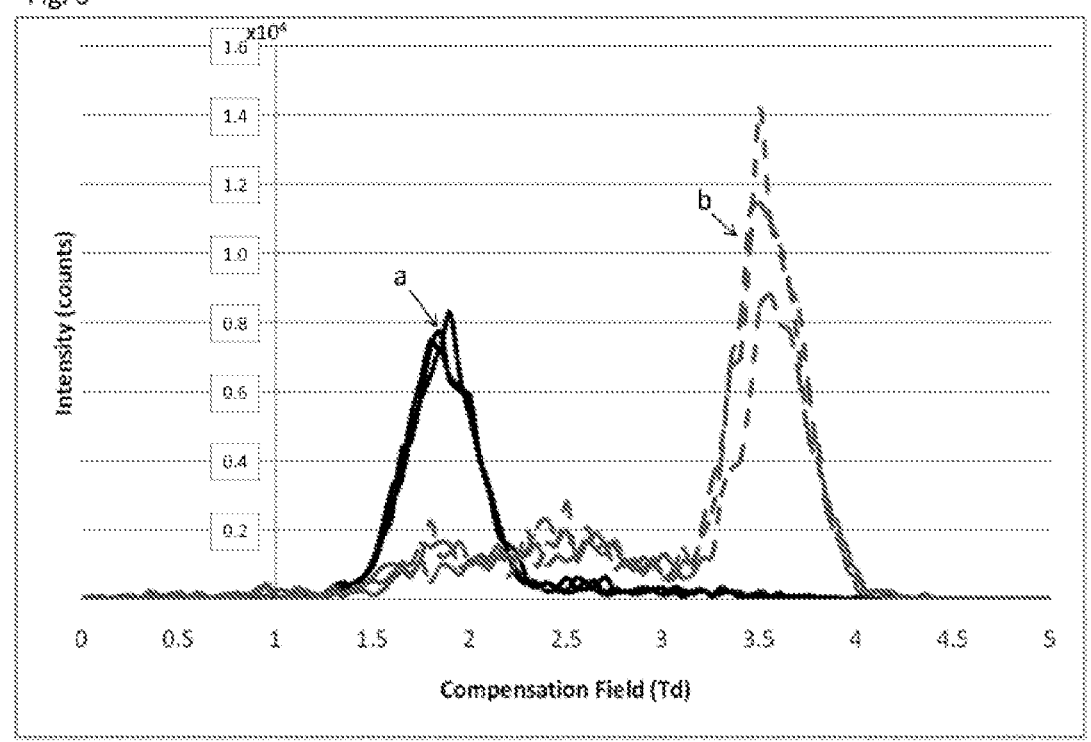
FIG. 3 shows the UltraFAIMS separation of 25-hydroxyvitamin D3 and 3-epi-25-hydroxyvitamin D3 as [M+Na]+ ions, according to Example 1.1 (a) and 1.1 (b) of Table 1. Both obtained spectra are superimposed. The x-axis shows compensation field (CF) in Townsends (Td). The y-axis shows signal intensity in counts. Signal (a) belongs to the Na+ adduct of 25-hydroxyvitamin D3 and signal (b) to the Na+ adduct of 3-epi-25hydroxyvitamin.
Figure 5:
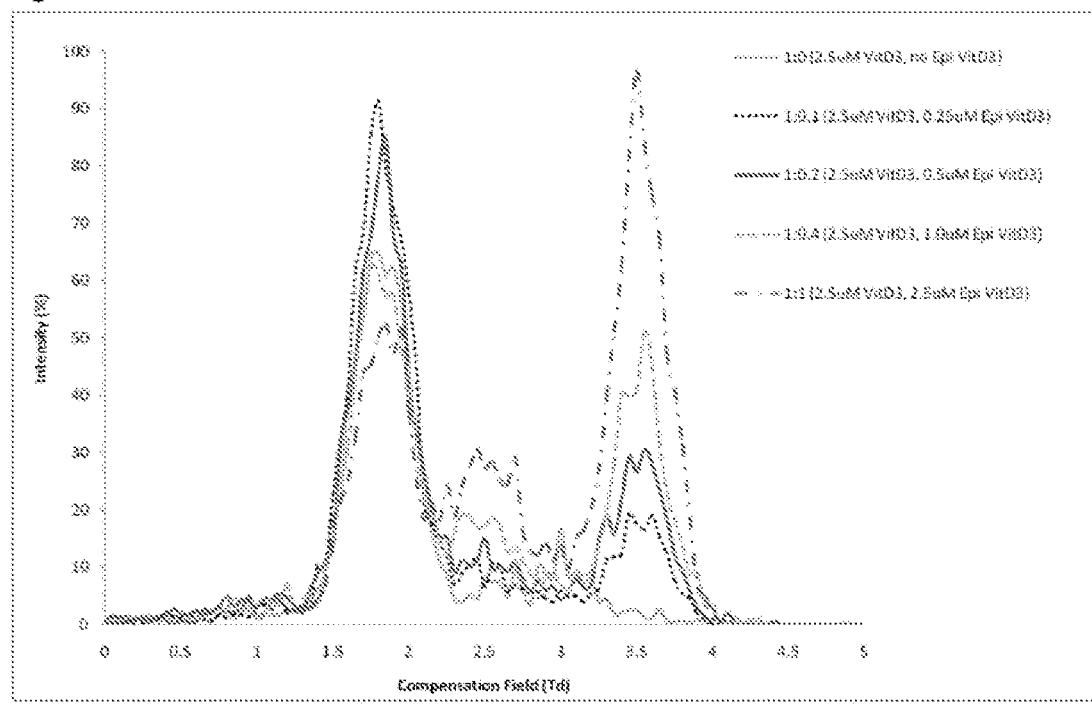
FIG. 5 shows the UltraFAIMS separation of 25-hydroxyvitamin D3 and 3-epi-25-hydroxyvitamin D3, as [M+Na]$^+$ ions, according to Example 1.2 to 1.6 of Table 1. Legend shows the starting concentrations of the individual samples (these were mixed together prior to analysis in a 1:1 ratio by volume) and the concentration ratio in the resulting mixtures.

The results of examples 1.1(a) and 1.1(b) are shown in FIG. 3 and the results of examples 1.2 to 1.6 are shown in FIG. 5, respectively.

Surprisingly even at lower TDs a baseline resolution of both analytes is obtained when the sodium adducts are observed.

Example 2

Vitamer D (Analysis with ABSciex Qtrap)

Stock solutions of 25-hydroxyvitamin D3 (25OHD3) and 25-hydroxyvitamin D3-3-epimer (epi-25OHD3) were prepared in methanol at 50 ug/mL. Working solutions were then prepared by diluting each metabolite to a final concentration of 5 ug/mL with methanol.

Example 2.1

In example 2.1 the working solutions also contained 100 uM sodium acetate. The metabolites were analyzed by direct infusion separately at a flow rate of 10 uL/min. The ABSciex Qtrap 6500 and Selexion DMS cell were operated under the following conditions: spray voltage 5,000 V, source gas 1 with 10 psi, source gas 2 with 0 psi, curtain gas with 25 psi, temperature 0° C., declustering potential 62 V, entrance potential 10 V, collision exit cell potential 21 V, DMS temperature low, modifier none, separation voltage 4,500 V, and resolution enhancement low. The compensation voltage (COV) was ramped between −10 to 30 V in 0.5 V increments while performing Q3 full scans from m/z 200 to 600 (sum 3 spectra).

Example 2.2

In example 2.2 the working solutions were analyzed in an automated fashion using an Agilent Infinity 2900 HPLC system for flow injection analysis. A volume of 5 μL was injected online where it was mixed with mobile phase and flushed through a 150×2.1 mm C18 column. The mobile phase was 300 μL/min of 10% 1 mM salt solution (see table) in water and 90% methanol; therefore, the effective working salt concentration was 100 μM before ion mobility analysis. The samples had virtually no retention on the column and were detected in 0.5 min peak widths upon injection into the mass spectrometer. The ABSciex Qtrap 6500 and Selexion DMS cell were operated under the following conditions: spray voltage 5,500 V, source gas 1 with 8 psi, source gas 2 with 15 psi, curtain gas with 10 psi, temperature 300° C., de-clustering potential 130 V, entrance potential 10 V, collision exit cell potential 21 V, DMS temperature low, modifier none, separation voltage 3,800 or 4,000 V, and resolution enhancement low. The compensation voltage (COV) was stepped between 2 to 18 V in 2 V increments while performing Q3 SIM multiple ion scans. Total ion chromatograms (TIC) were generated for each unique COV value and the relative peak area was plotted as a function of COV value to generate COV curves.

Figure 6:
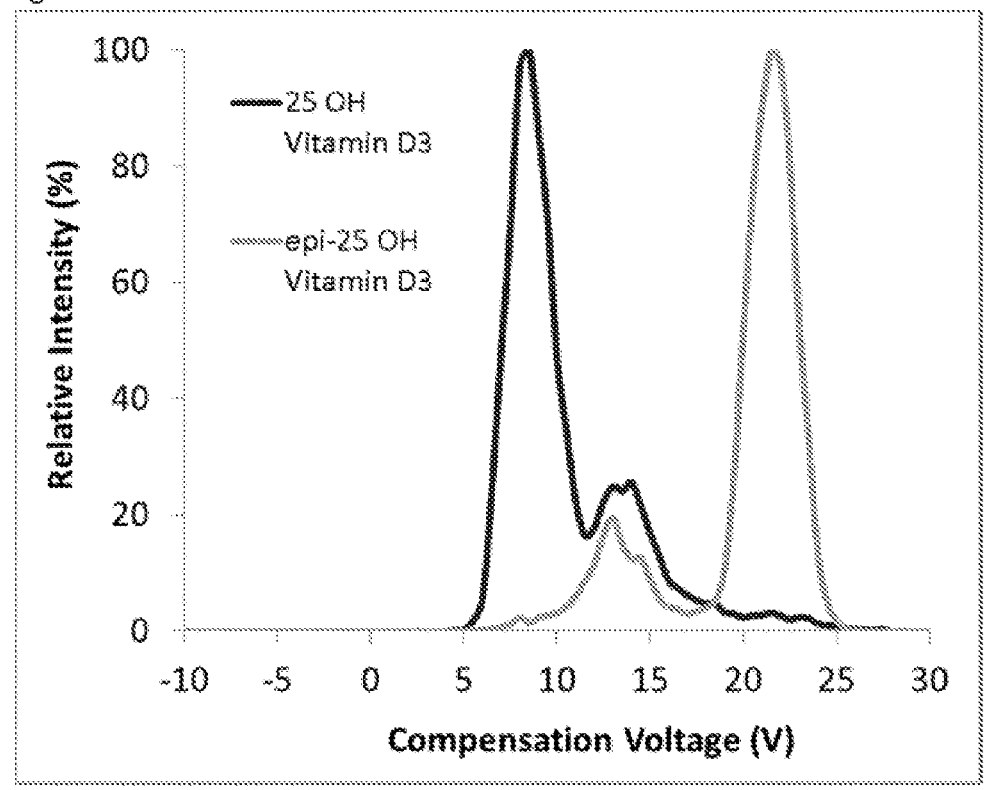
FIG. 6 shows the Selexlon DMS separation of 25-hydroxy vitamin D3 (25 OH Vitamin D3) and 3-epi-25-hydroxy vitamin D3 (epi-25 OH Vitamin D3) with sodium acetate on a AB Sciex QTrap 6500 instrument according to example 2.1. The x-axis shows the compensation voltage and the y-axis shows the relative signal intensity.
Figure 7:
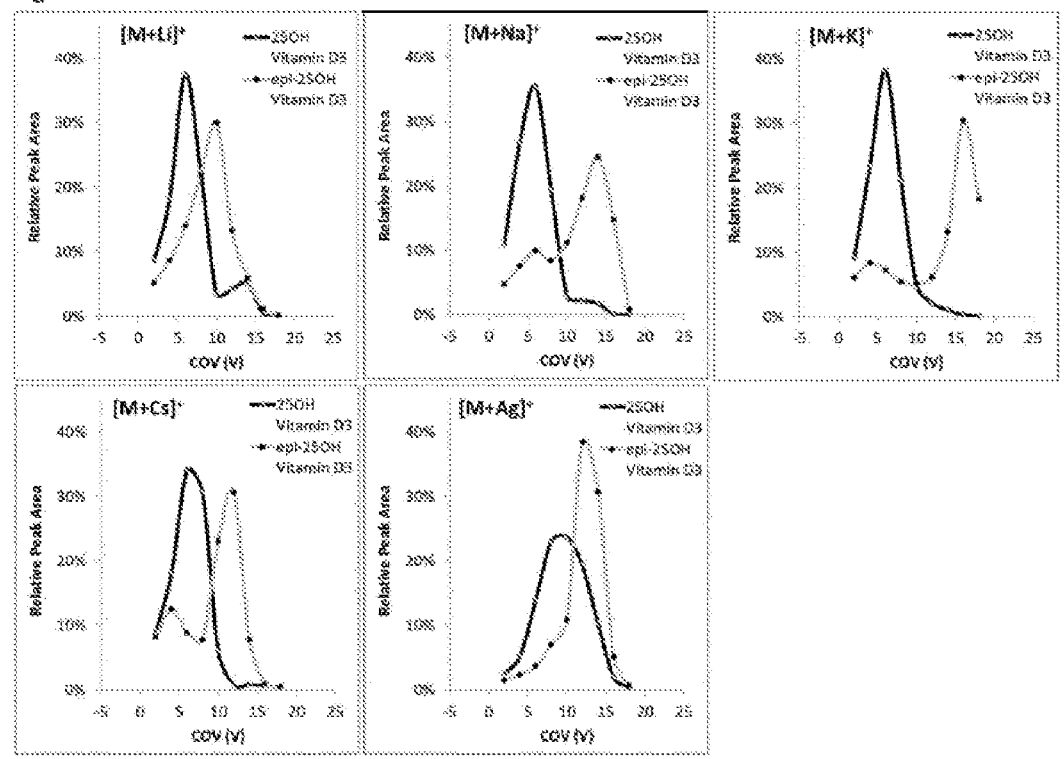
FIG. 7 shows the Selexlon DMS separation of 25-hydroxy vitamin D3 (25 OH Vitamin D3, black curve, grey dots) and 3-epi-25-hydroxy vitamin D3 (epi-25OH Vitamin D3, grey curve, black dots) with five different salt additives on a AB Sciex QTrap 6500 instrument according to example 2.2. The x-axis shows the compensation voltage and the y-axis shows the relative peak area. [M+Li]+: lithium formate (Table 2, 2.2.1 a+b), [M+NA]+: sodium acetate (Table 2, 2.2.2 a+b), [M+K]+: potassium chloride (Table 2, 2.2.3 a+b), [M+Cs]+: cesium formate (Table 2, 2.2.4 a+b), and [M+Ag]+: silver nitrate (Table 2, 2.2.5 a+b).
Figure 13:
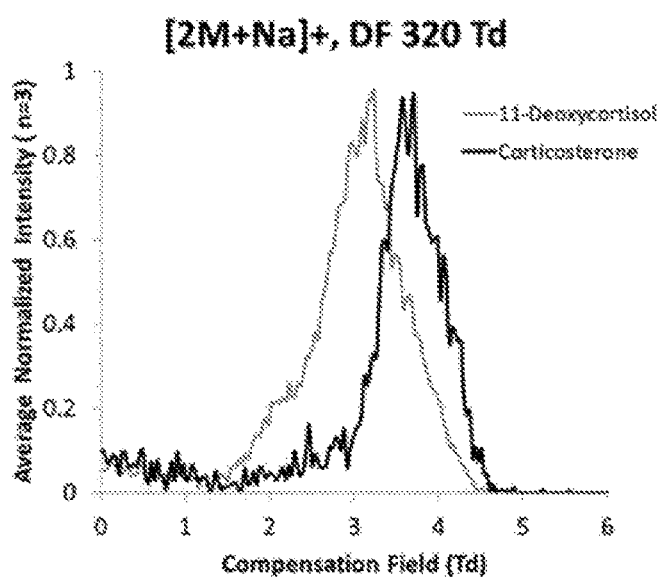
FIG. 13 shows the UltraFAIMS separation of corticosterone and 11-deoxycortisol with sodium acetate on an Owlstone UltraFAIMS T1 connected to a Thermo LTQ XL mass spectrometer. The x-axis shows the compensation field and the y-axis shows the average normalized intensity of three measurements.

The experimental details are summarized in Table 2 and the results are given in FIGS. 6 and 7. Under optimal conditions a baseline separation is obtained (FIG. 13) between 25-Hydroxy-Vitamin D3 (see 2.1 (a); Table 2; FIG. 13 black curve) and 3-epi-25-Hydroxy-Vitamin D3 (see 2.1 (b); Table 2; FIG. 13 grey curve. Additionally, the ion mobility separation is demonstrated for the following salt pairs (Table 2 and FIG. 7): lithium formate (2.2.1 a+b), sodium acetate (2.2.2 a+b), potassium chloride (2.2.3 a+b), cesium formate (2.2.4 a+b), and silver nitrate (2.2.5 a+b).

TABLE 2

| Example | Concentration of 25-Hydroxy-Vitamin D3 [μmol/L] | Concentration 3-epi-25-Hydroxy-Vitamin D3 [μmol/L] | Salt Content | Separation Voltage (V) | See FIG. |
|---|---|---|---|---|---|
| 2.1 (a) | 12.5 | 0 | 100 μM sodium acetate | 4,500 | 6 |
| 2.1 (b) | 0 | 12.5 | 100 μM sodium acetate | 4,500 | 6 |
| 2.2.1 (a) | 12.5 | 0 | 100 μM lithium formate | 4,000 | 7 |

TABLE 2-continued

| Example | Concentration of 25-Hydroxy-Vitamin D3 [μmol/L] | Concentration 3-epi-25-Hydroxy-Vitamin D3 [μmol/L] | Salt Content | Separation Voltage (V) | See FIG. |
|---|---|---|---|---|---|
| 2.2.1 (b) | 0 | 12.5 | 100 μM lithium formate | 4,000 | 7 |
| 2.2.2 (a) | 12.5 | 0 | 100 μM sodium acetate | 4,000 | 7 |
| 2.2.2 (b) | 0 | 12.5 | 100 μM sodium acetate | 4,000 | 7 |
| 2.2.3 (a) | 12.5 | 0 | 100 μM potassium chloride | 4,000 | 7 |
| 2.2.3 (b) | 0 | 12.5 | 100 μM potassium chloride | 4,000 | 7 |
| 2.2.4 (a) | 12.5 | 0 | 100 μM cesium formate | 4,000 | 7 |
| 2.2.4 (b) | 0 | 12.5 | 100 μM cesium formate | 4,000 | 7 |
| 2.2.5 (a) | 12.5 | 0 | 100 μM silver nitrate | 3,800 | 7 |
| 2.2.5 (b) | 0 | 12.5 | 100 μM silver nitrate | 3,800 | 7 |

Example 3

Amphetamine (Analysis with AB Sciex Qtrap)

Stock solutions of corticosterone, 11-deoxycortisol and 21-deoxycortisol were prepared in methanol at 0.5-1.5 mg/mL. A reference stock solution of 1 mg/mL amphetamine-d6 (d+1) in methanol was obtained from Cerilliant (A-045). Working solutions for the steroids and amphetamine mixture were then prepared by diluting each to a final concentration of 2 ug/mL in water:methanol (1:1). Samples analyzed by direct fusion were also spiked with a final concentration of 100 uM of the respective salt.

The working solutions were analyzed either in an automated fashion using an Agilent Infinity 2900 HPLC system for flow injection analysis or by direct infusion with a syringe pump. For the automated flow injection analysis, a volume of 20 uL was directly injected into the ion mobility mass spectrometer by a 150 uL/min flow rate of water:methanol (70:30). The respective salt solution was prepared at 1 mM and pumped at 10 uL/min into the sample flow via a T-Piece fitting; therefore, the effective working salt concentration was 63 uM before ion mobility analysis. The ABSciex Qtrap 6500 and Selexion DMS cell were operated under the following conditions for the steroid separation: spray voltage 5,500 V, source gas 1 with 8 psi, source gas 2 with 15 psi, curtain gas with 10 psi, temperature 300° C., declustering potential 130 V, entrance potential 10 V, collision exit cell potential 21 V, DMS temperature low, modifier none, separation voltage 4,000 V, and resolution enhancement medium. For the amphetamine analysis the conditions were as follows: spray voltage 4,500 V, source gas 1 with 8 psi, source gas 2 with 5 psi, curtain gas with 10 psi, temperature 100° C., declustering potential 20 V, entrance potential 10 V, collision exit cell potential 21 V, DMS temperature low, modifier none, separation voltage 3,800 or 4,000 V, and resolution enhancement off.

The compensation voltage (COV) was scanned while performing Q3 SIM multiple ion scans. Total ion chromatograms (TIC) were generated for each unique COV value and the relative peak area was plotted as a function of COV value to generate COV curves.

Figure 8:
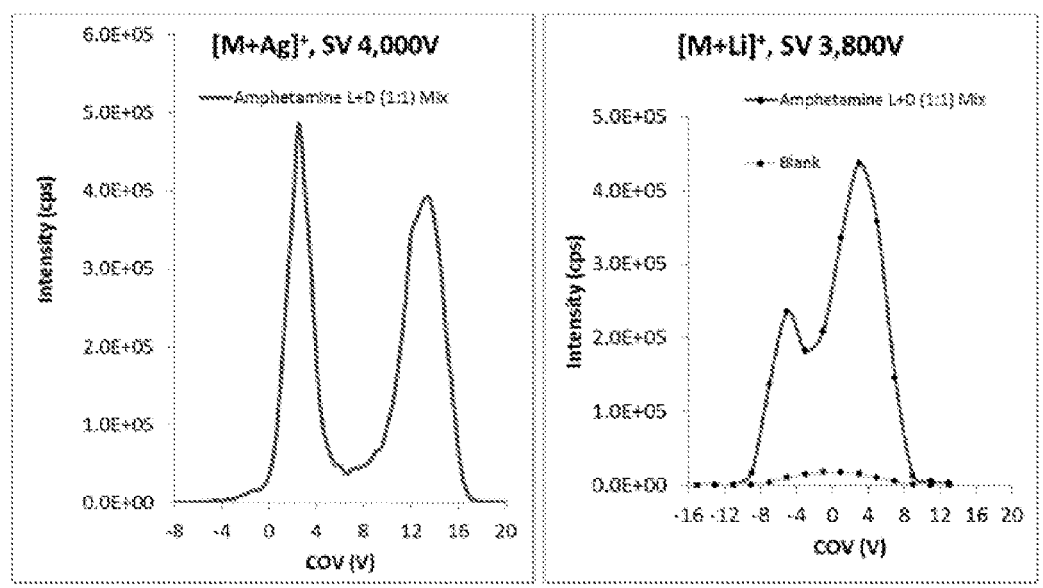
FIG. 8 shows the Selexlon DMS separation of 1-amphetamine-d6 and d-amphetamine-d6 with silver nitrate and lithium formate on a AB Sciex QTrap 6500 instrument. The x-axis shows the compensation voltage and the y-axis shows the absolute signal intensity.
Figure 9:
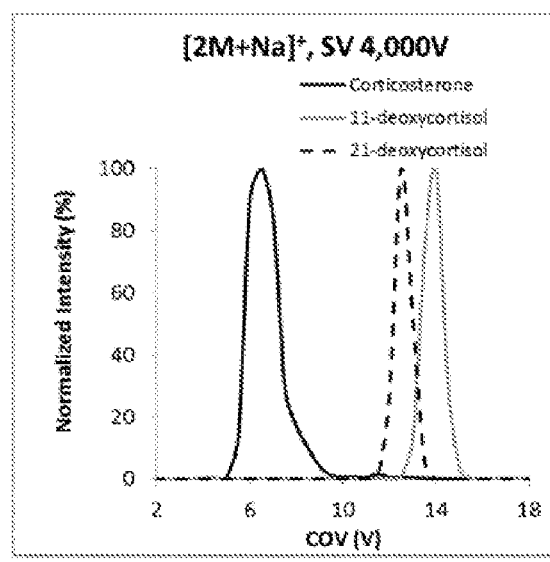
FIG. 9 shows the Selexlon DMS separation of corticosterone, 11-deoxycortisol and 21-deoxycortisol dimers formed by addition of sodium acetate using a AB Sciex QTrap 6500 instrument. The x-axis shows the compensation voltage and the y-axis shows the relative signal intensity.

The experimental details are summarized in Table 3 and the results are given in FIGS. 8 and 9.

TABLE 3

| Example | Substances | Concentration of each substance [μmol/L] | Salt Content | Separation Voltage (V) | See FIG. |
|---|---|---|---|---|---|
| 3 | 1-amphetamine-d6 d-amphetamine-d6 | 7 | 100 μM silver chloride | 4,000 | 8 |
| 3 | 1-amphetamine-d6 d-amphetamine-d6 | 7 | 63 μM lithium acetate | 3,800 | 8 |
| 3 | corticosterone, 11-deoxycortisol 21-deoxycortisol | 6 | 100 μM sodium acetate | 4,000 | 9 |

Example 4

Vancomycin B (Analysis with ABSciex Qtrap)

Solutions of Vancomycin B and its isoforms CDP1 (CDP1 contains CDP Major (CDPM) and CDP minor (CDPm)) were prepared. Mixture containing Vancomycin and CDP Major (CDPM) and CDP minor (CDPm) were then prepared at 10 µg/ml in water.

The solutions were analyzed using an Agilent Infinity 2900 HPLC system for fast, low resolution separation to separate the CDPM and CDPm metabolites. The mobile phases were water (A) and methanol (B) and a 4 minute fast gradient program was used (10-65% B) at 500 uL/min for the separation on a Zorbax C8 HPLC column. The respective salt solution was prepared at 1 mM and pumped at 10 uL/min into the sample flow via a T-Piece fitting; therefore, the effective working salt concentration was 20 uM before ion mobility analysis. The ABSciex Qtrap 6500 and Selexion DMS cell were operated under the following conditions: spray voltage 5,500 V, source gas 1 with 40 psi, source gas 2 with 50 psi, curtain gas with 35 psi, temperature 450° C., declustering potential 130 V, entrance potential 10 V, collision exit cell potential 21 V, DMS temperature low, modifier none, separation voltage 4,000 V, and resolution enhancement low.

The compensation voltage (COV) was scanned while performing Q3 SIM multiple ion scans. Average signal intensity across the chromatographic peak were plotted for each COV value to construct the curves.

Figure 11:
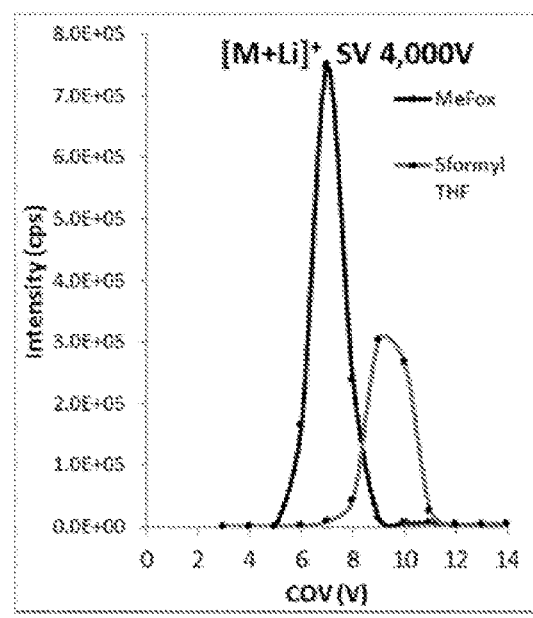
FIG. 11*a* shows the Selexlon DMS separation of 4a-hydroxy-5-methylTHF and 5-methyltetrahydrofolate with lithium formate on a AB Sciex QTrap 6500 instrument. The x-axis shows the compensation voltage and the y-axis shows the absolute signal intensity.
FIG. 11*b* shows the Selexlon DMS separation of 4a-hydroxy-5-methylTHF and 5-methyltetrahydrofolate with sodium acetate on a AB Sciex QTrap 6500 instrument. The x-axis shows the compensation voltage and the y-axis shows the absolute signal intensity.
FIG. 11*e* shows the Selexlon DMS separation of 4a-hydroxy-5-methylTHF and 5-methyltetrahydrofolate with potassium chloride on a AB Sciex QTrap 6500 instrument. The x-axis shows the compensation voltage and the y-axis shows the absolute signal intensity.
Figure 11:
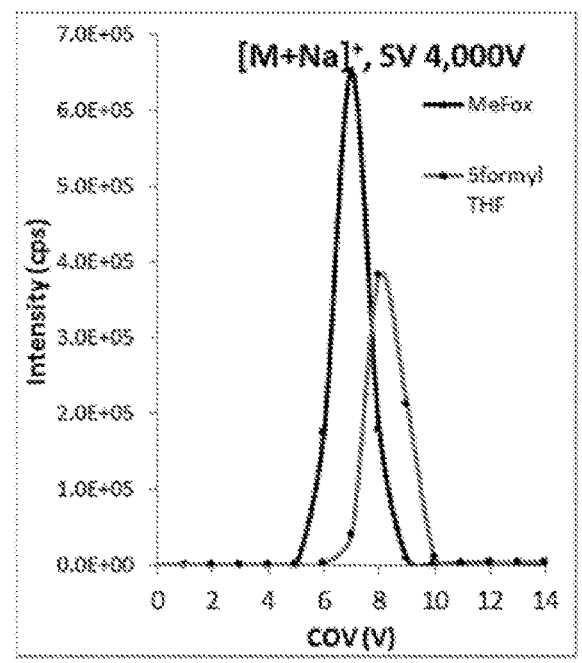
Figure 11C:
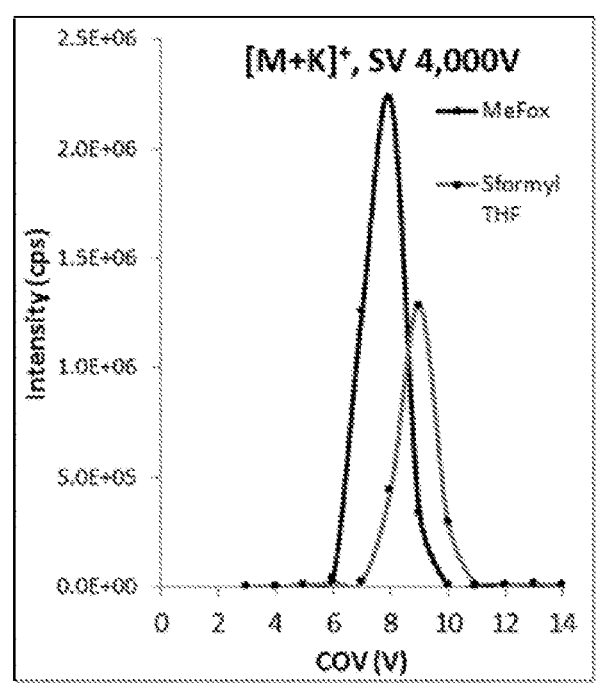

The experimental details are summarized in Table 4 and the results are given in FIGS. 11a to c.

TABLE 4

| Example | Substances | Concentration of Each Substance [µmol/L] | Salt Content | Separation Voltage (V) | See FIG. |
|---|---|---|---|---|---|
| 5a | 4a-hydroxy-5-methylTHF 5-methyltetrahydrofolate | 2.3 | 100 µM lithium formate | 4,000 | 11a |
| 5b | 4a-hydroxy-5-methylTHF 5-methyltetrahydrofolate | 2.3 | 63 µM sodium acetate | 4,000 | 11b |
| 5c | 4a-hydroxy-5-methylTHF 5-methyltetrahydrofolate | 2.3 | 100 µM potassium chloride | 4,000 | 11c | ion mobility analysis. The ABSciex Qtrap 6500 and Selexion DMS cell were operated under the following conditions: spray voltage 4,500 V, source gas 1 with 17 psi, source gas 2 with 20 psi, curtain gas with 20 psi, temperature 300° C., declustering potential 135 V, entrance potential 10 V, collision exit cell potential 22 V, DMS temperature low, modifier none, separation voltage 4,000 V, and resolution enhancement low.

The compensation voltage (COV) was scanned while performing Q3 SIM multiple ion scans. Average signal intensity across the chromatographic peak were plotted as a function of COV value to construct the curves.

Figure 10A:
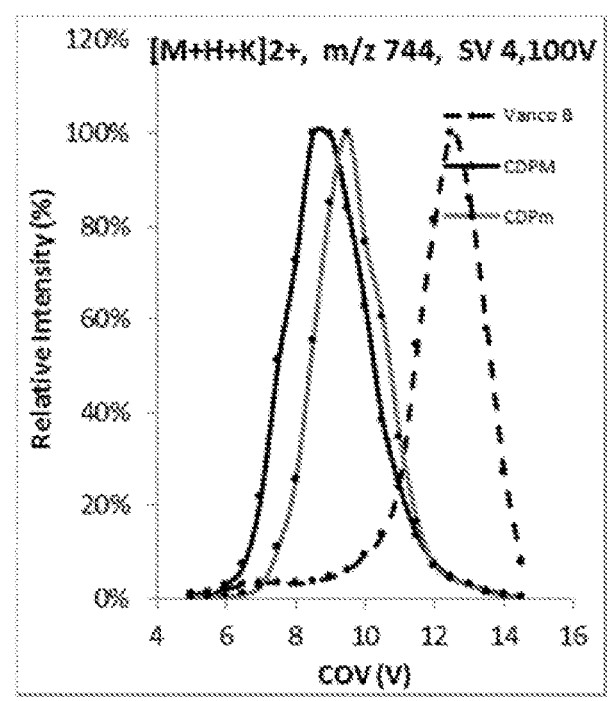
FIG. 10*a* shows the Selexlon DMS separation Vancomycin B and its isoforms CDP1 (CDP1 contains CDP Major (CDPM) and CDP minor (CDPm)) with potassium ions (potassium chloride) on a AB Sciex QTrap 6500 instrument. The x-axis shows the compensation voltage and the y-axis shows the absolute signal intensity. The best result can be achieved with Potassium Chloride when compared to FIGS. 10*b* and 10*c*.
Figure 10B:
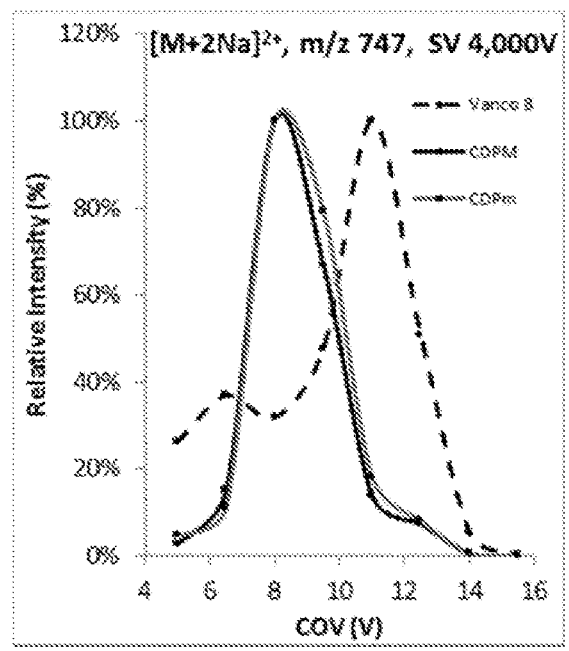
FIG. 10*b* shows the Selexlon DMS separation Vancomycin B and its isoforms CDP1 (CDPI contains CDP Major (CDPM) and CDP minor (CDPm)) with sodium ions on a AB Sciex QTrap 6500 instrument. The x-axis shows the compensation voltage and the y-axis shows the absolute signal intensity. The best result can be achieved with Potassium Chloride when compared to FIGS. 10*b* and 10*c*.
Figure 10C:
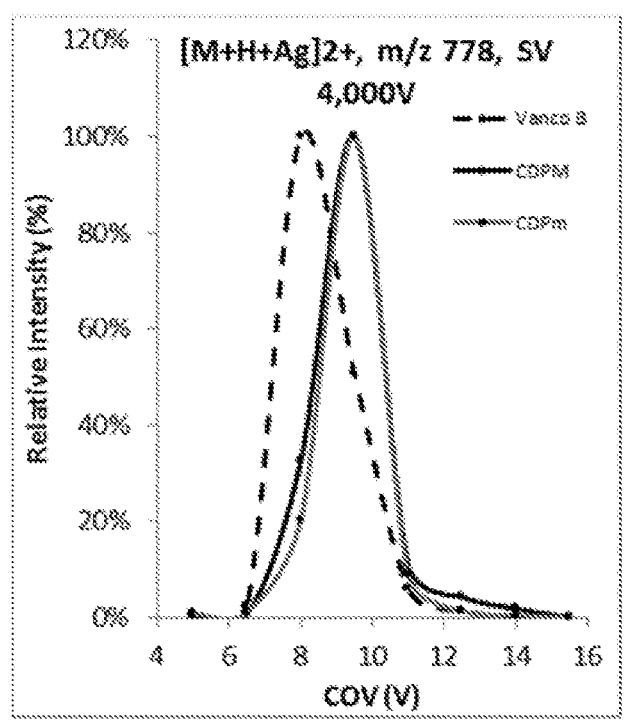
FIG. 10*c* shows the Selexlon DMS separation Vancomycin B and its isoforms CDPI (CDP1 contains CDP Major (CDPM) and CDP minor (CDPm)) with silver ions on a AB Sciex QTrap 6500 instrument. The x-axis shows the compensation voltage and the y-axis shows the absolute signal intensity. The best result can be achieved with Potassium Chloride when compared to FIGS. 1*b* and 10*c*.

Further experimental details and the respective results are given in FIGS. 10a-10c.

Example 5

Folate (Separation 4a-hydroxy-5-methylTHF and 5-methyltetrahydrofolate) Analysis on ABSciex Qtrap Stock solutions of 4a-hydroxy-5-methylTHF (MeFox) and 5-methyltetrahydrofolate (5formyl-THF) were prepared at 100 ug/mL in water with 0.1% sodium ascorbate. Working solutions were prepared by diluting to 1 ug/mL in water.

The working solutions were analyzed using an Agilent Infinity 2900 HPLC system for fast, low resolution separation to remove impurities before ion mobility mass spectrometry analysis. The isocratic mobile phase was 89.5% water, 10% methanol and 0.5% acetic acid. The respective salt solution was prepared at 1 mM and pumped at 10 uL/min into the sample flow via a T-Piece fitting; therefore, the effective working salt concentration was 63 uM before ion mobility analysis. The ABSciex Qtrap 6500 and Selexion DMS cell were operated under the following conditions: spray voltage 5,500 V, source gas 1 with 40 psi, source gas 2 with 50 psi, curtain gas with 35 psi, temperature 450° C., declustering potential 130 V, entrance potential 10 V, collision exit cell potential 21 V, DMS temperature low, modifier none, separation voltage 4,000 V, and resolution enhancement low.

The compensation voltage (COV) was scanned while performing Q3 SIM multiple ion scans. Average signal intensity across the chromatographic peak were plotted for each COV value to construct the curves.

The experimental details are summarized in Table 4 and the results are given in FIGS. 11a to c.

Example 6

Amphetamine and Corticosterone/11-deoxycortisol

Stock solutions of corticosterone and 21-deoxycortisol were prepared in methanol at 0.5-1.5 mg/mL. A reference stock solution of 1 mg/mL amphetamine-d6 (d+1) in methanol was obtained from Cerilliant (A-045). Working solutions for the steroids and amphetamine mixture were then prepared by diluting each to a final concentration of 10 µg/mL in water:methanol (1:1) containing 1 mM of the respective salt solution (silver nitrate or sodium acetate).

Figure 12:
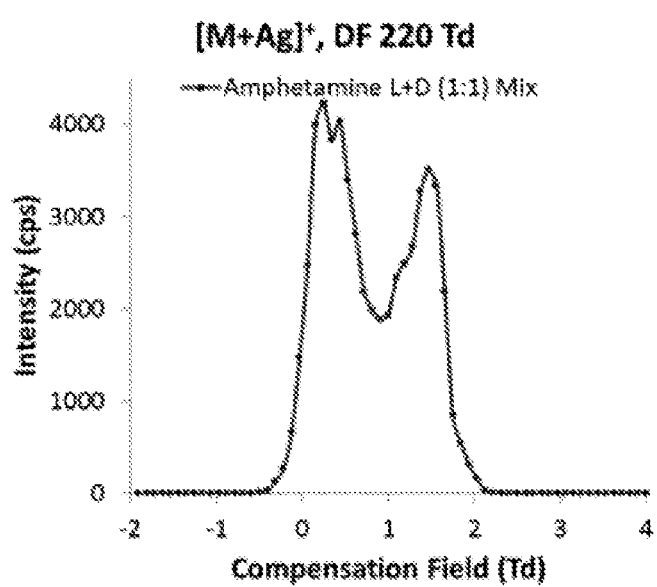
FIG. 12 shows the UltraFAIMS separation of 1-amphetamine-d6 and d-amphetamine-d6 with silver chloride on an Owlstone UltraFAIMS T1 connected to a Thermo LTQ XL mass spectrometer. The x-axis shows the compensation field and the y-axis shows the absolute signal intensity.

The working samples were analyzed individually by direct infusion using a flow rate of 5 µL/min. The hardware used was an Owlstone UltraFAIMS T1 connected to a Thermo LTQ XL mass spectrometer. The heated transfer capillary temperature was adjusted between 50-400° C. and the gas flows were adjusted between 0-20 PSI in order to optimize peak shape and selectivity for the desired separation. During a single experiment a fixed dispersion field (DF) was applied and the compensation field (CF) was ramped to sweep out the ions. Meanwhile the MS system acquired ion intensity in single ion monitoring (SIM) mode of the desired ionic species. Finally, the ion intensity was plotted as a function of the compensation field to show the ion mobility separation. (FIGS. 12a and b)

TABLE 5

| Example | Substances | Concentration of Each Substance [µmol/L] | Salt Content | Separation Field (Td) | See FIG. |
|---|---|---|---|---|---|
| 6a | l-amphetamine-d6 d-amphetamine-d6 | 35 | 1000 µM silver chloride | 220 | 12 |
| 6b | corticosterone, 11-deoxycortisol | 30 | 1000 µM sodium acetate | 320 | 13 |

LIST OF REFERENCE NUMBERS 110 system for quantifying the amount of at least two analytes in a sample
112 raw sample
114 sample preparation device
116 chromatographic device
118 Sample
120 salt
122 addition of salt
124 ion mobility separator
126 ionizer
128 FAIMS device
130 electric field
132 Pair of parallel electrodes (drift tube)
134 high-voltage periods
136 low-voltage periods
138 outlet opening
140 drift path of an unbalanced ion
142 drift path of a balanced ion
144 device for monitoring an output of the ion mobility separator
146 ion mobility spectrometer
148 output flow
150 mass spectrometer

The invention claimed is:

1. A method of quantifying the amount of at least two analytes A1 and A2 comprised in a sample, comprising:
    (a) adding at least one salt (S) being a monovalent cation of an alkaline metal or a transition metal or of an organic compound, and wherein, when the salt is a monovalent cation of an organic compound, the cation is selected from the group consisting of pyridine, pyrrolindin, imidazole and morpholin to at least a portion (P1) of the sample comprising the at least two analytes A1 and A2,
    (b) ionizing in the presence of the at least one salt (S) at least a portion of the sample according to (a) thereby forming an analyte flow comprising the analytes A1 and A2 in ionized form,
    (c) separating the ionized analytes A1 and A2 from each other by using at least one ion mobility separator, wherein the analyte flow according to (b) at least partially passes through the ion mobility separator, and
    (d) quantifying the amount of the separated ionized analytes obtained according to (c), wherein A1 is a pharmaceutically active compound C or derivative thereof and A2 is an epimer of C, and wherein A1 has a log P value of greater than 0.

2. The method according to claim 1, wherein said log P value of A1 is the octanol/water partitioning coefficient of A1.

3. The method according to claim 1, wherein A1 is a vitamin D and wherein A2 is 3-epi-25-hydroxy vitamin D3.

4. The method according to claim 1, wherein the sample is a blood, plasma or serum sample derived from a raw sample comprising the analytes A1 and A2 and matrix constituents, and wherein the method further comprises removing at least part of the matrix constituents before performing step (a) to give the sample according to (a).

5. The method according to claim 1, wherein the salt (S) is a salt of a monovalent cation selected from the group consisting of Li+, Na+, K+, Rb+, Cs+, Ag+, Cu+, Ni+, Mn+, pyridinium and mixtures of two or more thereof.

6. The method according to claim 1, wherein the sample according to (a) comprises the added salt (S) in a concentration in the range of from 25 micromol/L to 2 mmol/L.

7. The method according to claim 1, wherein in (a) at least one further additive is added.

8. The method according to claim 1, wherein in (a) at least one acid is additionally added.

9. The method according to claim 1, wherein step (b) comprises using at least one ionizer, wherein the ionizer is used for at least partially ionizing the sample and thereby generating the analyte flow before or during entering the ion mobility separator.

10. The method according to claim 1, wherein the ion mobility separator is a field-asymmetric waveform ion mobility separator.

11. The method according to claim 1, wherein the ion mobility separator comprises at least one ion mobility spectrometer or wherein the ion mobility separator is part of at least one ion mobility spectrum spectrometer, wherein the ion mobility spectrum spectrometer comprises at least one field-asymmetric waveform ion mobility spectrometer.

12. The method according to claim 1, wherein step (c) further comprises using at least one mass spectrometer for analyzing an output flow of the ion mobility separator.

13. The method according to claim 12, wherein the mass spectrometer comprises one or more of: a tandem mass spectrometer, an ion trap mass spectrometer, a time-of-flight mass spectrometer, a Fourier transformation mass spectrometer, an orbitrap mass spectrometer, a quadrupole mass spectrometer.

14. A method of using at least one salt (S) as a modifier in a process for quantifying the amount of at least two analytes A1 and A2 comprised in a sample by ion mobility spectrometry, the method comprising ionizing the sample in the presence of the at least one salt (S), wherein the salt is a monovalent cation of an alkaline metal or a transition metal or of an organic compound, and wherein, when the salt is a monovalent cation of an organic compound, the cation is selected from the group consisting of pyridine, pyrrolindin, imidazole and morpholin, wherein A1 is a pharmaceutically active compound C or a derivative thereof and A2 is an epimer of C, and wherein A1 has a log P value of greater than 0.

15. The method according to claim 1, wherein A1 has a log P value of greater than 2.

16. The method according to claim 1, wherein A1 is 25-hydroxy-vitamin D3 and wherein A2 is 3-epi-25-hydroxy vitamin D3.

17. The method according to claim 1, wherein in (a) at least one further additive is added selected from the group consisting of acetonitrile, methanol, ethanol, propanol and butanol.

18. The method according to claim 1, wherein in (a) at least formic acid is additionally added.

19. The method according to claim 1, wherein A1 is a vitamin D and wherein A2 is 3-epi-25-hydroxy vitamin D3, and wherein the salt (S) is a salt of a monovalent cation selected from the group consisting of Li+, Na+, K+, Rb+, Cs+, Ag+, Cu+, Ni+, Mn+, pyridinium and mixtures of two or more thereof.

20. The method according to claim 14, wherein A1 has a log P value of greater than 2.

21. A method of quantifying the amount of at least two analytes A1 and A2 comprised in a sample, comprising:

(a) adding at least one salt (S) being a monovalent cation selected from the group consisting of Li+, Na+, K+, Rb+, Cs+, Ag+, Cu+, Ni+, Mn+, pyridinium and combinations thereof to at least a portion (P1) of the sample comprising the at least two analytes A1 and A2, (b) ionizing in the presence of the at least one salt (S) at least a portion of the sample according to (a) thereby forming an analyte flow comprising the analytes A1 and A2 in ionized form, (c) separating the ionized analytes A1 and A2 from each other by using at least one ion mobility separator, wherein the analyte flow according to (b) at least partially passes through the ion mobility separator, (d) quantifying the amount of the separated ionized analytes obtained according to (c), wherein A1 is a pharmaceutically active compound C or derivative thereof and A2 is an epimer of C, and wherein A1 has a log P value in the range of from 0 to 12.

* * * * *